US009770564B2

(12) United States Patent
Goodman et al.

(10) Patent No.: US 9,770,564 B2
(45) Date of Patent: Sep. 26, 2017

(54) MEDICANT DELIVERY SYSTEM

(71) Applicant: Chong Corporation, Minneapolis, MN (US)

(72) Inventors: Jack Goodman, Ann Arbor, MI (US); William O'Neill, Maple Grove, MN (US); Alexander ChinHak Chong, St. Louis Park, MN (US); William P Bartkowski, Edina, MN (US); Peter Joseph Kovach, Fridley, MN (US); Larry Gawain Linde, Andover, MN (US); Randy Eugene Berg, Coon Rapids, MN (US)

(73) Assignee: CHONG CORPORATION, Minneapolis, MN (US)

(*) Notice: Subject to any disclaimer, the term of this patent is extended or adjusted under 35 U.S.C. 154(b) by 0 days.

(21) Appl. No.: 15/220,323

(22) Filed: Jul. 26, 2016

(65) Prior Publication Data

US 2016/0331915 A1 Nov. 17, 2016

Related U.S. Application Data

(60) Division of application No. 13/453,939, filed on Apr. 23, 2012, now Pat. No. 9,399,110, which is a (Continued)

(51) Int. Cl.
*A61M 16/10* (2006.01)
*A61M 15/06* (2006.01)
(Continued)

(52) U.S. Cl.
CPC .......... *A61M 15/06* (2013.01); *A24F 47/008* (2013.01); *A61M 15/0065* (2013.01); (Continued)

(58) Field of Classification Search
CPC ......... A24B 13/02; A24B 15/00; A24B 15/12; A24B 15/18; A24B 15/42; A24C 5/3406; (Continued)

(56) References Cited

U.S. PATENT DOCUMENTS 4,228,925 A 10/1980 Mendelovich
4,520,864 A 6/1985 Katagiri et al.
(Continued)

FOREIGN PATENT DOCUMENTS

CA 2562581 A1 10/2005
CN 2047485 11/1989
(Continued)

OTHER PUBLICATIONS

Materials Manual, Non-Metal—Jul. 1985.
(Continued)

*Primary Examiner* — Annette Dixon
(74) *Attorney, Agent, or Firm* — Cisio & Thomas, LLP

(57) ABSTRACT

An improved medicant delivery system is disclosed wherein the carrier for the medicant is a fluid that can be atomized or vaporized by exposure to heat. The system provides for repeatable dose of medicant, can be stored in any orientation, and/or has an ability to maximize energy efficiency.

6 Claims, 26 Drawing Sheets

Related U.S. Application Data continuation-in-part of application No. 13/044,355, filed on Mar. 9, 2011, now Pat. No. 8,903,228.

(60) Provisional application No. 61/478,460, filed on Apr. 22, 2011.

(51) Int. Cl.
*A24F 47/00* (2006.01)
*A61M 15/00* (2006.01)
*F22B 1/28* (2006.01)

(52) U.S. Cl.
CPC .... *A61M 15/0091* (2013.01); *A61M 16/1075* (2013.01); *F22B 1/282* (2013.01); *A61M 2205/3372* (2013.01)

(58) Field of Classification Search
CPC .. A24D 1/00; A24D 1/002; A24F 1/00; A24F 13/00; A24F 47/00; A24F 47/004; A24F 47/006; A24F 47/008; A24F 5/00; A61M 11/00; A61M 11/007; A61M 11/04; A61M 11/041; A61M 11/042; A61M 15/0021; A61M 15/06; A61M 16/16; A61M 16/202; A61M 2205/3317; A61M 2205/3368; A61M 2205/8262; A61M 2209/02
USPC ............. 128/200.11–200.24, 200.14, 202.21, 128/203.12, 203.15, 203.16, 203.17, 128/203.26, 203.27, 204.13, 204.17, 128/204.18, 204.21
See application file for complete search history.

(56) References Cited

U.S. PATENT DOCUMENTS

| | | | |
|---|---|---|---|
| 4,531,912 A | 7/1985 | Schuss et al. | |
| 4,641,053 A | 2/1987 | Takeda | |
| 4,735,217 A | 4/1988 | Gerth et al. | |
| 4,848,374 A | 7/1989 | Chard et al. | |
| 4,945,929 A | 8/1990 | Egilmex | |
| 4,945,931 A | 8/1990 | Gori | |
| 5,042,470 A | 8/1991 | Kanesaka | |
| 5,076,292 A | 12/1991 | Ridings et al. | |
| 5,080,114 A | 1/1992 | Rudolph et al. | |
| 5,095,921 A | 3/1992 | Losee et al. | |
| 5,144,962 A * | 9/1992 | Counts | A24F 47/008 128/200.14 |
| 5,190,060 A | 3/1993 | Gerding et al. | |
| 5,203,355 A | 4/1993 | Clearman et al. | |
| 5,234,008 A | 8/1993 | Fagg | |
| 5,240,012 A | 8/1993 | Ehrman et al. | |
| 5,240,016 A | 8/1993 | Nichols et al. | |
| 5,247,947 A | 9/1993 | Clearman et al. | |
| 5,322,075 A | 6/1994 | Deevi et al. | |
| 5,389,078 A | 2/1995 | Zalesky et al. | |
| 5,474,059 A | 12/1995 | Cooper | |
| 5,486,362 A | 1/1996 | Kitchell et al. | |
| 5,505,214 A * | 4/1996 | Collins | A24F 47/008 128/202.21 |
| 5,551,416 A | 9/1996 | Stipson | |
| 5,666,978 A | 9/1997 | Counts et al. | |
| 5,743,251 A | 4/1998 | Howell et al. | |
| 5,894,841 A | 4/1999 | Voges et al. | |
| 5,928,189 A | 7/1999 | Phillips et al. | |
| 5,944,025 A | 8/1999 | Waltermire et al. | |
| 6,040,560 A | 3/2000 | Fleischlauer et al. | |
| 6,178,969 B1 | 1/2001 | St. Charles | |
| 6,196,218 B1 | 3/2001 | Voges | |
| 6,234,167 B1 | 5/2001 | Cox et al. | |
| 6,357,671 B1 | 3/2002 | Cewers | |
| 6,443,146 B1 | 9/2002 | Voges | |
| 6,513,524 B1 | 2/2003 | Storz | |
| 6,532,965 B1 | 3/2003 | Abhulimen et al. | |
| 6,845,216 B2 | 1/2005 | Shuster et al. | |
| 6,854,461 B2 | 2/2005 | Nichols et al. | |
| 7,238,057 B2 | 7/2007 | Baranowski | |
| 7,364,427 B2 | 4/2008 | Huang et al. | |
| 7,448,919 B2 | 11/2008 | Baranowski | |
| 7,651,010 B2 | 1/2010 | Orzech et al. | |
| 7,726,320 B2 | 6/2010 | Robinson et al. | |
| 7,832,410 B2 | 11/2010 | Hon | |
| 7,845,359 B2 | 12/2010 | Montaser | |
| 2003/0033055 A1 | 2/2003 | McRae et al. | |
| 2004/0031495 A1 | 2/2004 | Steinberg | |
| 2005/0016550 A1 | 1/2005 | Katase | |
| 2005/0170303 A1 | 8/2005 | Huang et al. | |
| 2006/0047368 A1 | 3/2006 | Maharajh et al. | |
| 2006/0166564 A1 | 7/2006 | Baranowski | |
| 2006/0196518 A1 | 9/2006 | Hon | |
| 2006/0204598 A1 | 9/2006 | Thompson | |
| 2006/0260626 A1 | 11/2006 | Luan et al. | |
| 2007/0167084 A1 | 7/2007 | Baranowski | |
| 2007/0267031 A1 | 11/2007 | Hon | |
| 2007/0280652 A1 | 12/2007 | Williams | |
| 2008/0060663 A1 | 3/2008 | Hamade et al. | |
| 2008/0092912 A1 * | 4/2008 | Robinson | A24F 47/008 131/200 |
| 2008/0166303 A1 | 7/2008 | Tamarkin et al. | |
| 2008/0173300 A1 | 7/2008 | Justman | |
| 2008/0230052 A1 | 9/2008 | Montaser | |
| 2008/0241255 A1 | 10/2008 | Rose et al. | |
| 2008/0247892 A1 | 10/2008 | Kawasumi | |
| 2008/0257367 A1 | 10/2008 | Paterno et al. | |
| 2008/0276947 A1 | 11/2008 | Martzel | |
| 2008/0315829 A1 | 12/2008 | Jones et al. | |
| 2009/0095311 A1 | 4/2009 | Han | |
| 2009/0118331 A1 | 5/2009 | Crooks et al. | |
| 2009/0126745 A1 | 5/2009 | Hon | |
| 2010/0031968 A1 | 2/2010 | Sheikh et al. | |
| 2010/0037903 A1 | 2/2010 | Coleman, III et al. | |
| 2010/0186739 A1 | 7/2010 | Kronestedt et al. | |
| 2010/0200006 A1 | 8/2010 | Robinson | |
| 2010/0200008 A1 | 8/2010 | Taieb | |
| 2010/0236546 A1 | 9/2010 | Yamada et al. | |
| 2010/0242979 A1 | 9/2010 | Pan | |
| 2010/0268171 A1 | 10/2010 | Moller | |
| 2011/0005535 A1 | 1/2011 | Xiu | |
| 2011/0011396 A1 | 1/2011 | Fang | |
| 2011/0036346 A1 | 2/2011 | Cohen et al. | |
| 2011/0041858 A1 | 2/2011 | Montaser | |
| 2012/0111346 A1 | 5/2012 | Rinker et al. | |

FOREIGN PATENT DOCUMENTS

| | | |
|---|---|---|
| CN | 89207339 | 11/1989 |
| CN | 1135860 | 11/1996 |
| CN | 2293957 Y | 10/1998 |
| CN | 1252961 | 5/2000 |
| CN | 1284493 | 2/2001 |
| CN | 1106812 | 4/2003 |
| CN | 1530041 | 9/2004 |
| CN | 2643681 Y | 9/2004 |
| CN | 2648836 Y | 10/2004 |
| CN | 1541577 | 11/2004 |
| CN | 1575673 | 2/2005 |
| CN | 2719043 Y | 8/2005 |
| CN | 2777995 Y | 5/2006 |
| CN | 201379072 Y | 11/2006 |
| CN | 1942114 A | 4/2007 |
| CN | 200966824 Y | 10/2007 |
| CN | 101084801 A | 12/2007 |
| CN | 201067079 Y | 6/2008 |
| CN | 201079011 Y | 7/2008 |
| CN | 201273820 Y | 7/2009 |
| CN | 1196660 A | 3/2010 |
| DE | 10051792 A1 | 5/2002 |
| EP | 0295122 A2 | 12/1988 |
| EP | 0342538 A2 | 5/1989 |
| EP | 0545186 A2 | 6/1993 |
| EP | 0824927 A2 | 2/1998 |
| EP | 0845220 A1 | 6/1998 |

(56) References Cited

FOREIGN PATENT DOCUMENTS

| | | |
|---|---|---|
| EP | 0893071 A1 | 1/1999 |
| EP | 0970627 A1 | 1/2000 |
| EP | 1618803 A1 | 1/2006 |
| EP | 1736065 A1 | 12/2006 |
| EP | 1731228 | 8/2010 |
| FR | 1537026 | 8/1968 |
| GB | 1083761 | 9/1967 |
| GB | 1528391 A1 | 10/1978 |
| JP | 60009462 | 1/1985 |
| JP | 64-000498 U | 1/1989 |
| JP | 07-506999 | 5/1993 |
| JP | 06-114105 A | 4/1994 |
| JP | 09-075058 A | 3/1997 |
| UA | 47514 | 7/2002 |
| WO | 97/48293 A1 | 12/1997 |
| WO | 00/49901 | 8/2000 |
| WO | 00/50111 | 8/2000 |
| WO | 03012565 | 2/2003 |
| WO | 03/022364 | 3/2003 |
| WO | 03/022364 A1 | 3/2003 |
| WO | 03/034847 A1 | 5/2003 |
| WO | 03034847 | 5/2003 |
| WO | 03/055486 | 7/2003 |
| WO | 03/101454 | 12/2003 |
| WO | 04/001407 | 12/2003 |
| WO | 2004/080216 | 9/2004 |
| WO | 2004/095955 | 11/2004 |
| WO | 2005/099494 | 10/2005 |
| WO | 2006/082571 | 8/2006 |
| WO | 2007/078273 | 7/2007 |
| WO | 2007/131449 | 11/2007 |
| WO | 2007/131450 | 11/2007 |
| WO | 2008/055423 | 5/2008 |
| WO | 2008/077271 | 7/2008 |
| WO | 2008/130813 | 10/2008 |
| WO | 2009112182 | 9/2009 |
| WO | 2009/118085 | 10/2009 |
| WO | 2009/135729 | 11/2009 |
| WO | 2010/052323 | 5/2010 |
| WO | 2010/091593 | 8/2010 |
| WO | 2010/145805 | 12/2010 |
| WO | 2011/010334 | 1/2011 |
| WO | WO 2011009920 | 1/2011 |

OTHER PUBLICATIONS

Intro Selecting Using Electronic Components Feb. 24, 2006.
Manual Electric Engineers Mar. 2000.
Manual Mechanical Designers Jan. 2002.
"What is a MOSFET, what does it look like, and how does it work?" May 24, 2004 www.techPowerUp.com.
International Search Report for PCT/GB0204766 dated Jan. 20, 2003.
Wikipedia_Lobelia, Last modified Feb. 28, 2012, Retrieved from the Internet: <http://en.wikipedia.org/wiki/Lobelia>.
International Search Report for PCT/US2010/45806 dated Sep. 29, 2010.
International Search Report for PCT/US2010/045804 dated Oct. 14, 2010.
Chinese Patent Office, International Search Report for PCT/CN2004/000182, dated Jun. 10, 2004.
Chinese Patent Office, International Search Report for PCT/CN2005/000337, dated Jul. 14, 2005.

* cited by examiner

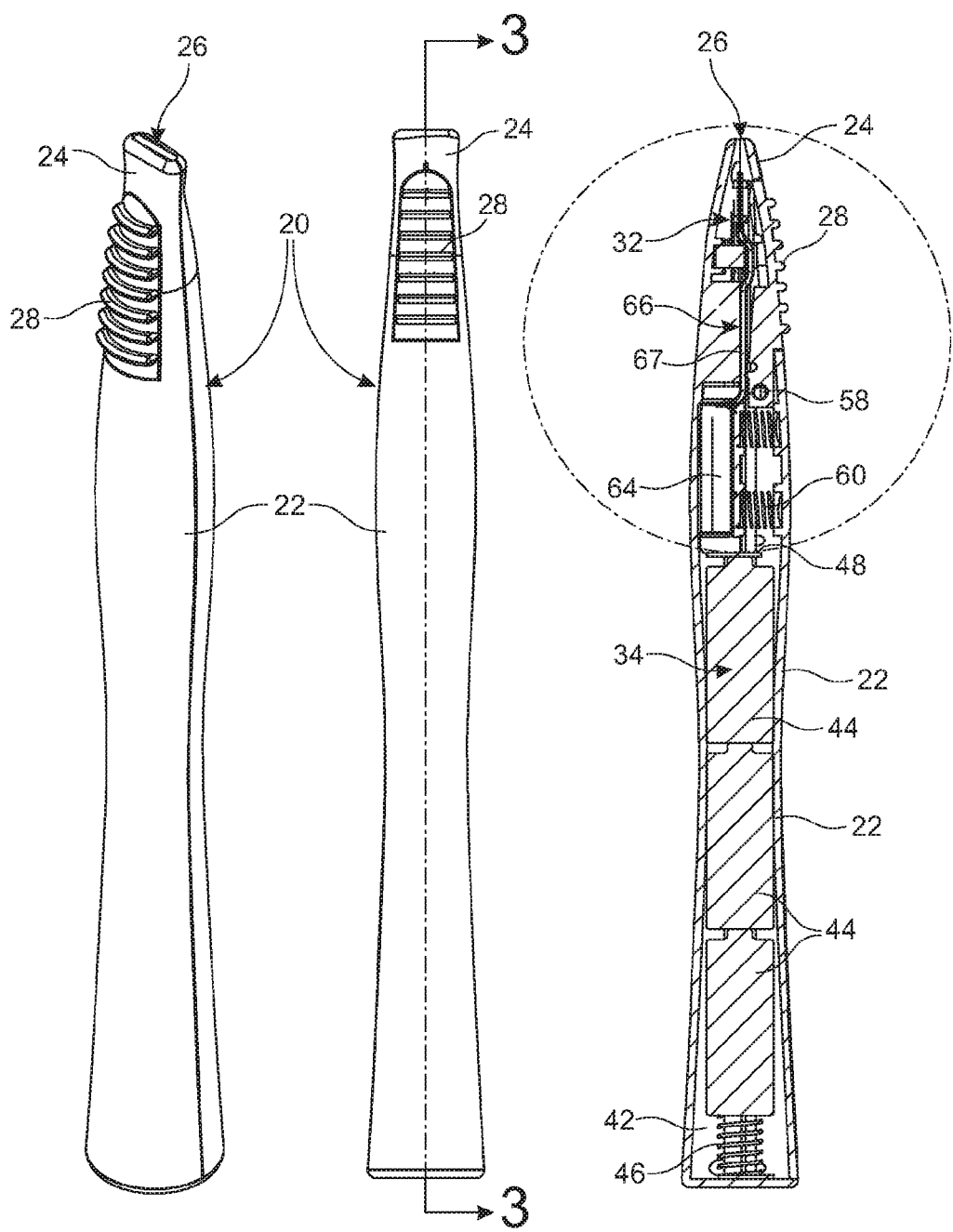

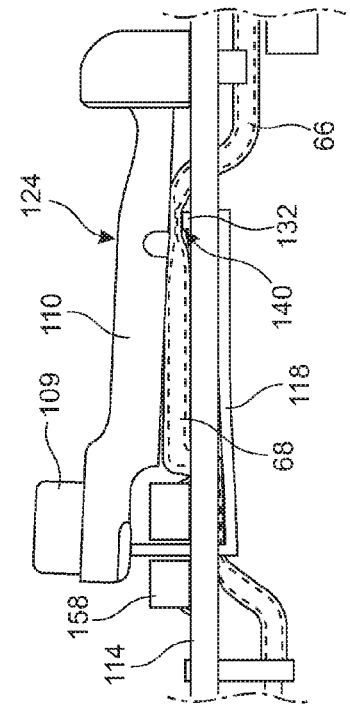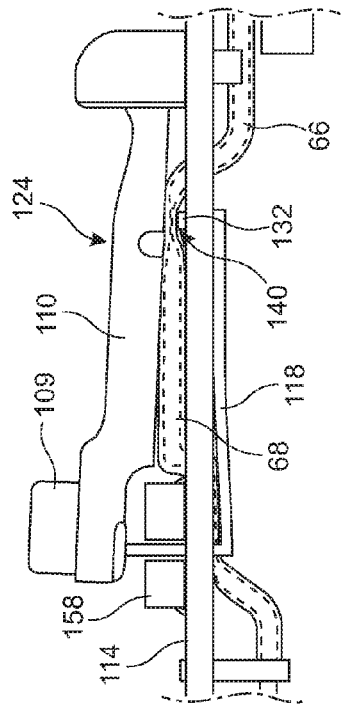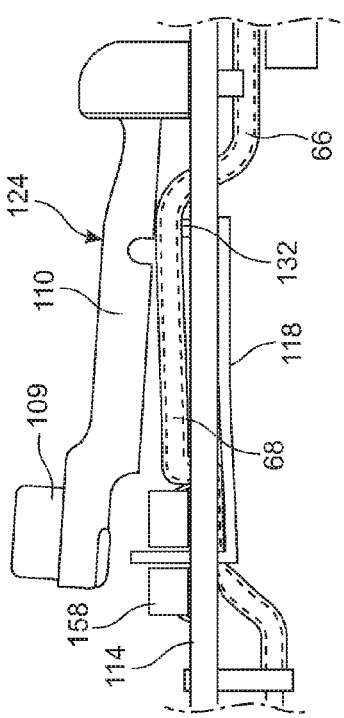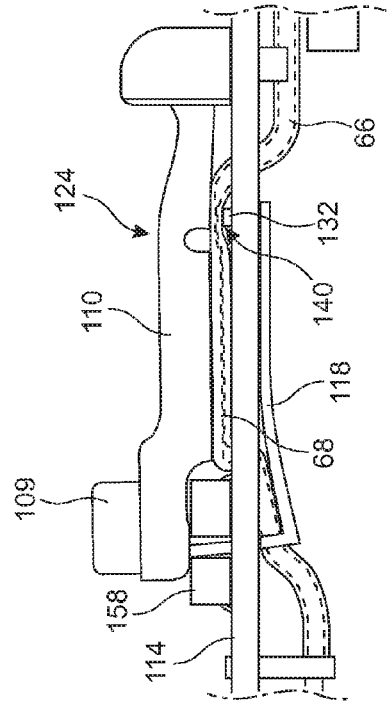
Fig. 10
Fig. 11
Fig. 12
Fig. 13

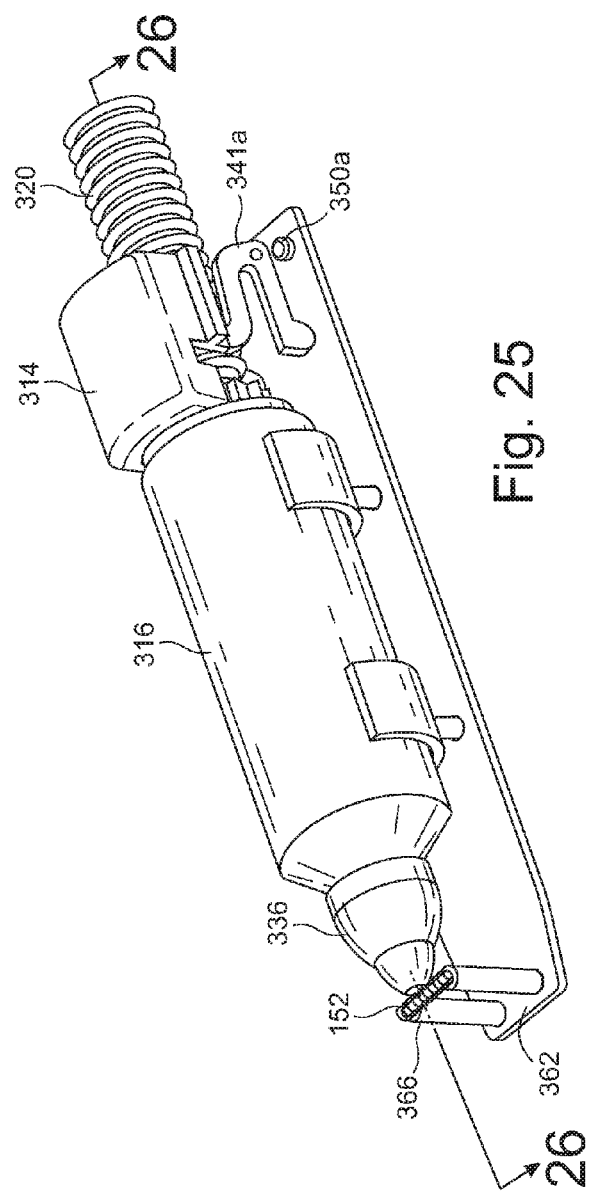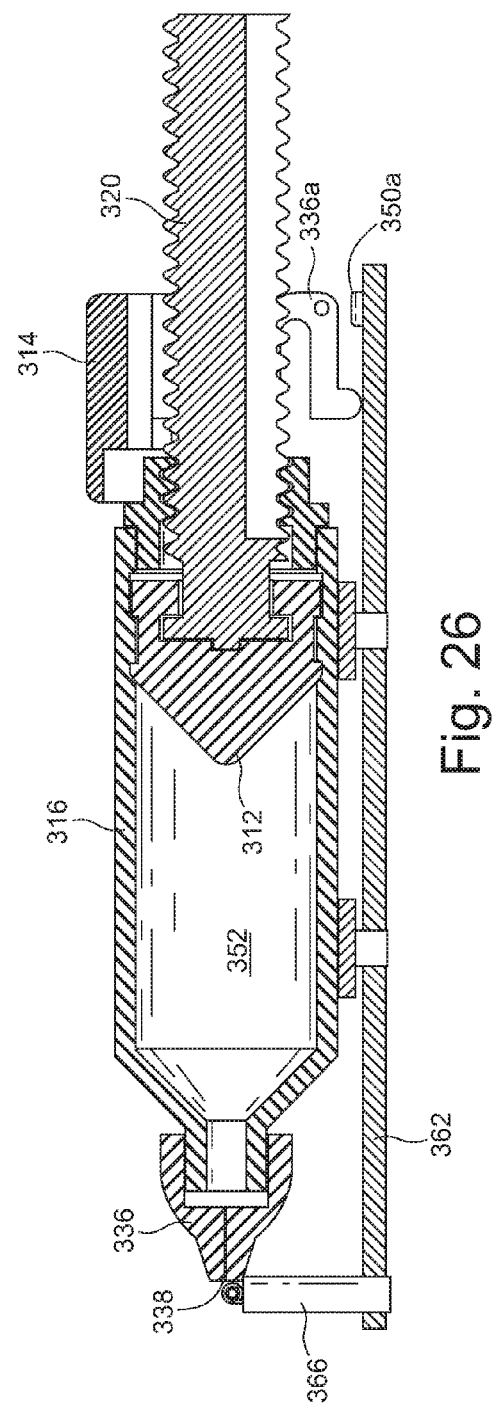

MEDICANT DELIVERY SYSTEM

CROSS-REFERENCE TO RELATED APPLICATION

This patent application is a divisional application of U.S. patent application Ser. No. 13/453,939, filed Apr. 23, 2012, entitled "Medicant Delivery System," now U.S. Pat. No. 9,399,110, which is a continuation-in-part application of U.S. patent application Ser. No. 13/044,355, filed Mar. 9, 2011, entitled "Vapor Delivery Devices and Methods," now U.S. Pat. No. 8,903,228; U.S. patent application Ser. No. 13/453,939 also claims the benefit of U.S. Provisional Patent Application No. 61/478,460, filed Apr. 22, 2011, entitled "Atomizing Medicant Delivery System," which applications are incorporated in their entirety here by this reference.

TECHNICAL FIELD

This invention relates to devices and methods for vaporizing a liquid for inhalation. More specifically, the invention relates to providing a device and method for controlling, metering and measuring precise volumes of fluid vaporized and the vapor produced by a hand-held vaporizing device each time the device is engaged by its user that is reliable and safer to use than current devices relying on lithium ion chemistry.

BACKGROUND

Various hand-held, personal vaporizing devices are currently available. Some of these have been specifically designed to produce a nicotine-infused vapor for the purpose of serving, as an alternative to smoking, a traditional tobacco cigarette wherein the tobacco is ignited and the user inhales the smoke and its constituents—including the nicotine-a naturally occurring constituent of tobacco. Devices used for the purpose of cigarette alternatives produce a vapor devoid of most of the 4000+ chemicals and byproducts of tobacco smoke and, therefore, deliver nicotine to the user, through ingestion of the vapor, without most of the harm normally associated with tobacco smoke.

Unfortunately, disadvantages still remain in the design and performance of these vaporizing devices. For example, some devices are bulky or cumbersome to use as a transportable, hand-held device.

Other vaporizing devices are incapable of delivering precise, consistent, and reliable metered doses of the medicant. Current electronic atomization cigarettes do not provide for a method to control the consistency of the volume of liquid vaporized nor the volume of vapor produced and, as a result, cannot produce a measurable amount of nicotine on a per vaporization basis. There are certain circumstances and situations, including those where regulations might dictate, where it may well be required that these devices be capable of delivering vapor and its nicotine constituent in a manner that enables the amount of nicotine present in the vapor be measurable and consistently repeated with each and every engagement by the user. In addition to or in lieu of nicotine, a vaporizer might be used to deliver other substances to the user, including medicants. Similarly, a precise measured "dose" may be desired, or even required for these substances.

In addition, because some of the devices on the market use a liquid storage unit that is "open" to the atmosphere, some devices leak or fail to perform reliably unless the vaporizing device is maintained in an upright position during use, or during the packaging, shipping, and storage of the device. Furthermore, with such devices, the liquid may be subject to contamination, adulteration and/or evaporation under certain conditions.

Finally, most, if not all, current commercially available products use lithium chemistry batteries as their power source. This is primarily due to three factors: 1) the useful life of the battery; 2) the power needed to vaporize the fluid; and, 3) the requirement for a small compact device roughly the size of traditional tobacco products—i.e. cigarettes and cigars, or in on-tobacco or nicotine formulations, the need for compactness in order to be discretely employed by the user in circumstances where discretion is appropriate. Lithium chemistry batteries, however, are volatile, hazardous (both in that they can release noxious vapors as well as potential for explosion under certain conditions) and environmentally challenging with respect to storage, reliability, and disposability.

It is anticipated that the lithium chemistry power source of hand-held portable devices will become an issue for U.S. regulators, distributors, retailers, and consumers as the current product gets more widely distributed and used and as more uses for the devices are identified, manufactured, distributed, sold and consumed.

Therefore, there is still a need for a device and method for providing an improved hand-held vapor delivery system that reliably and consistently produces a repeatable metered dose of a medicant in a safe, efficient, and effective manner.

SUMMARY

In one aspect, a method and device for improving hand-held vapor delivery devices to generate reliable, consistent, repeatable metered doses of a medicament or medicant comprises a power control system utilizing an integrated circuit capable of determining and delivering the precise amount of power for the precise duration of time that is just enough to completely vaporize a predetermined volume of a liquid.

In another aspect, the method and device for an improved hand-held vapor delivery device may comprise a fluid delivery system, a vaporizing or atomizing system, and a power control system contained in a housing, wherein the fluid delivery system consistently, repeatably, and reliably delivers a precise metered dose to the atomizing system, and the power delivery system supplies just enough electrical power to the atomizing system to completely atomize or vaporize the exact volume of liquid delivered to the atomizing system.

In another aspect, the hand-held vapor delivery device has an ability to operate independent of orientation, and/or an ability to deliver a repeatable dose of medicant, and/or an ability to be stored in any orientation, and/or an ability to maximize energy efficiency.

In another aspect, the invention provides a device and method that enables vapor delivery devices to use more stable, more reliable, less environmentally hazardous, and safer sources of battery chemistry without significantly affecting the portability and discreteness of the devices.

BRIEF DESCRIPTION OF DRAWINGS

FIG. 1 is a perspective view of an embodiment of a medicant delivery device of the present invention.
FIG. 2 is a top view of the device shown in FIG. 1.
FIG. 3 is a section view taken along line 3-3 of FIG. 2.

FIGS. 10-13 are side views of the device shown in FIGS. 7-9 illustrating sequential steps of operation.

FIG. 25 is close-up isometric view of an embodiment of a fluid delivery system shown in FIG. 24.

FIG. 26 is a section view through line 26-26 of the fluid delivery system shown in FIG. 25.

DETAILED DESCRIPTION OF THE INVENTION

Figure 4:
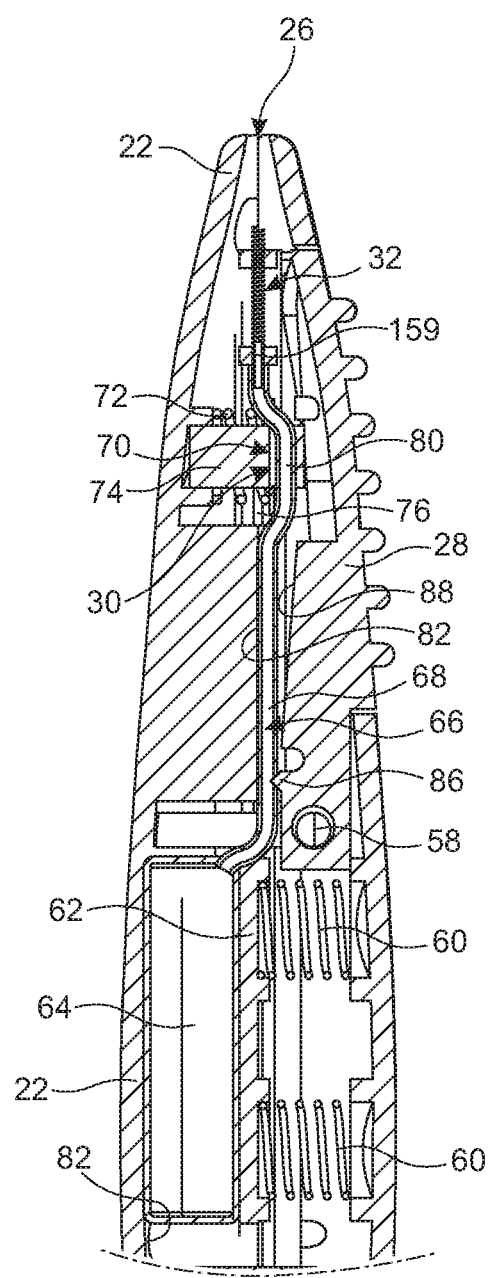
FIG. 4 is an enlarged detail section view of the upper section of the device shown in FIG. 3.

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

To improve the ability to meter a precise dose of a medicant in vapor form for inhalation from a vapor delivery device, the vapor delivery device requires either a power control system that can control the amount and duration of heat applied to a liquid form of the medicant, or a fluid delivery system that can accurately, consistently, and repeatably discharge a precise volume of a medicant. These two methods: (a) controlling the amount of heat applied to the liquid, and (b) controlling the volume of liquid to be vaporized, can be used alone or combination to improve the accuracy of the medicant "dose" provided by the vaporizer. As used in the claims, the term "medicant" means a medicament, medication, medicine, pharmaceutical, drug, and the like used for healing, treating, altering, improving, restoring, relieving, and/or curing a particular condition, disease, or mental or physical state, which includes the active ingredient or combination of active ingredients and inactive ingredients infused into an expedient or dissolved in some other carrier.

The amount and duration of the heat applied correlates with the amount of power supplied to the vapor delivery device. Therefore, in order to improve the functionality of current vapor delivery devices, the current devices must be implemented with a power control system that comprises a means for providing a precise amount of power from a power source to heat a heating element to a minimum required temperature that completely vaporizes a predetermined volume of a liquid. Based on the properties of a medicant, in particular, the expedient or carrier, the minimum required temperature to completely vaporize a predetermined volume can be calculated. By knowing the minimum temperature required to vaporize a predetermined volume of a medicant, energy resources can be conserved by not using more energy than is necessary, which is one of the problems with current devices.

The means for providing a precise amount of power from a power source to heat a heating element to a minimum required temperature to completely vaporize a predetermined volume of a liquid comprises a control circuit or integrated circuit 82 having a processor 500 that controls the power sent to a heating element 152 to ensure that only the necessary amount of power is provided to vaporize the specific volume discharged. Since the amount of power supplied to a heating element 152 correlates with the resistance through the heating element, the processor 500 may be programmed to monitor the resistance of the heating element 152 as a proxy for the amount of power being supplied to the heating element 152. Knowing the resistance, the processor 500 can govern the amount of power to supply to the heating element 152. Measuring the resistance at the heating element has several advantages. First, power may be accurately measured and maintained. Second, it measures the resultant voltage from the circuit, rather than measuring it from the battery, which conserves battery life. Third, it insures that vaporization remains constant, allowing for measured dosages irrespective of the life cycle of the battery and degradation of the heating element.

In some embodiments, the means for providing a precise amount of power may also comprise a boost converter that is a switched DC/DC convert, in conjunction with super capacitors 368a, 368b. The boost converter uses a charge converter that functions with an H bridge and inductor/capacitor system. By using the boost converter the charge current is limited to preserve the batteries and a much higher discharge current from the supercap is allowed, but for a shorter duration. By way of example only, it may take 3-5 seconds to charge but only 0.5 second to discharge. Thus, the battery may only see 100-200 mA load, but the capacitor might see 1 A or more. By utilizing this system, alkaline batteries 364 can be used, thereby improving the safety of this device.

A supercapacitor ("supercap") 368a, 368b is an electrochemical capacitor with relatively high energy density. Its energy density is typically hundreds of times greater than conventional electrolytic capacitors. A supercap 368a, 368b can store up to two orders of magnitude the capacitance a standard electrolytic capacitor can maintain.

The described invention circuitry charges a supercap 368a, 368b from a set of alkaline batteries 364 using a DC/DC boost converter. When charging a supercap 368a, 368b numerous parameters must be taken into consideration. For illustrative purposes, a 300 farad capacitor bank that is to be charged to 6V DC, using a 6V power source (4-1.5V AA batteries) capable of sourcing 1.2 A MAX current could be used. Note that a resistor can be used in this circuit to the current to a maximum amperage—e.g. 1 A, etc., as an additional control of the heating circuit.

To define how the invention charging circuitry works, the Ohm's law equation is used—Charge resistor value=6V/1 A=6 Ohms. This is determined using Ohm's law: R=E/I, where R is the resistance in ohms, E is the energy in volts, and I is the current amps.

To determine what it takes to charge the capacitor bank, 'Power' is utilized, which electrically is described as 'Wattage' This Power equation is described as:

Resistor Power=6V×1 A=6 W (Power=Voltage×Current)

Thus, in order to charge a 6V capacitor bank at 1 A with a 6V power supply (4 AA/AAA batteries), a 6 Ohm resistor with a wattage rating of 6 W or higher is needed. In certain designs, fewer batteries, such as one, two, or three, be used to supply sufficient power.

Using this approach, this invention solves the standard problem of battery life issues that current electronic cigarettes (e-cigarettes) have. Additionally, this approach provides the ability to maintain sufficient power to vaporize the liquid using standard alkaline chemistry batteries, which current e-cigarette devices are incapable of utilizing.

FIG. 37 shows a block diagram of the process. There is an energy or power source 600 that supplies the input power. This source can be one of several types but in general fits in two types. Type 1 may be a low power source not capable of the higher current to function directly. This type of power source requires additional conditioning to support full function, thus requires a power conversion stage 602 and a power storage stage 608. Type 2 may be a high current source that allows a direct drive of the vaporization element.

State or control logic 604, which may be dedicated logic or a processor, supplies the control, measurement and drive functions. One embodiment may use a Texas Instrument MSP430 processor, but this could be any processor or ASIC-like device. GPIO and AID functions may also be used to allow the measurement of either the current flow (direct drive) or voltage in the power storage (sup cap). When all conditions are met, the control logic 604 activates the discharge switch 610 to heat the vaporization element 612.

The ability to accurately measure and meter the power that energizes the vaporization element 612 allows the accurate metering of the vapor phase transition and dosage amounts. In the direct drive system the current and time of drive are used to compute and meter the energy that is used to heat the vaporization element 612. In the stored energy system the formula $\frac{1}{2}CV^2$ is used to compute the energy in the system and the desired end voltage to meter the energy used to heat the vaporization element 612, where C is the capacitance and V is the voltage.

An alternative to controlling the amount power would be to control the amount of time the heating element is energized as the power source begins to dissipate. The processor 500 can be configured to monitor the resistance and adjust the time the heating element remains on so as to completely vaporize a given volume of medicant.

In some embodiments, a flow switch 614 may be used to signal the requested start of a vaporization phase. When implemented into a vaporization device, the device may have a fluid delivery system (discussed below). The fluid delivery system deposits a required amount of fluid on the vaporization element 612 prior to activation of the flow switch 614.

In some embodiments, a fluid discharge activator 616 may be used to "wake up" the processor 604 and charge 606 the supercap 608 (in the stored energy system). In the direct drive system, the fluid discharge activator would be used to "wake" the processor 604 from an ultra-low power sleep mode. The fluid discharge actuator 616 may be a mechanical device to activate the system, such as a turn switch, a button, knob, lever, and the like.

In some embodiments, diodes 618, 620 may be used to indicate to the operator the status of the system operation. For example, one diode may be an LED 618 to signal when the vaporization element 612 is being driven. Another LED 620 may be used to blink specified patterns to indicate system status, e.g. power up, low battery, exhausted fluid state, or other system specific status states (i.e. max dosage per unit time, etc. . . . ). In other embodiments, a display, such as an LCD screen, may be used to show the system status or other information, such as the type of substance or medicant contained in the delivery device, the amount and/or doses remaining, the battery level, a user ID in case the device is lost, etc. A button or similar device could be used to actuate and scroll through the display.

In a Type 1 configuration (low current, alkaline batteries etc.) the charge current may be limited to preserve the battery lifecycle. In many batteries, if large amounts of current are drawn, it will significantly reduce the battery life or state of charge. Therefore, using the lower current draw from the batteries and the power storage stage 608 allows for a high current event without unduly draining the batteries.

In a Type 2 configuration, the power storage 608 can be used to extend the life of the battery (lithium polymer, lithium-ion) if desired. The power storage 608 also makes it easier to very accurately meter the precise amount of energy into the vaporization element 612 with a simple voltage measurement. Accurately metering precise amounts of energy into the vaporization element can be done with a voltage and current measurement but it is harder to accurately measure current than to measure voltage. Thus, it may be advantageous to use a simpler-voltage only process.

An additional power saving feature that is shared with the control logic 604 and the power conversion 602, namely, the power state (on switch) of the system. This power saving feature with the power state can be accomplished via either an ultra-low power mode of the conversion/cpu or a power disconnect/latch function. This is used to extend the operation life of the device after the first use.

Figure 15:
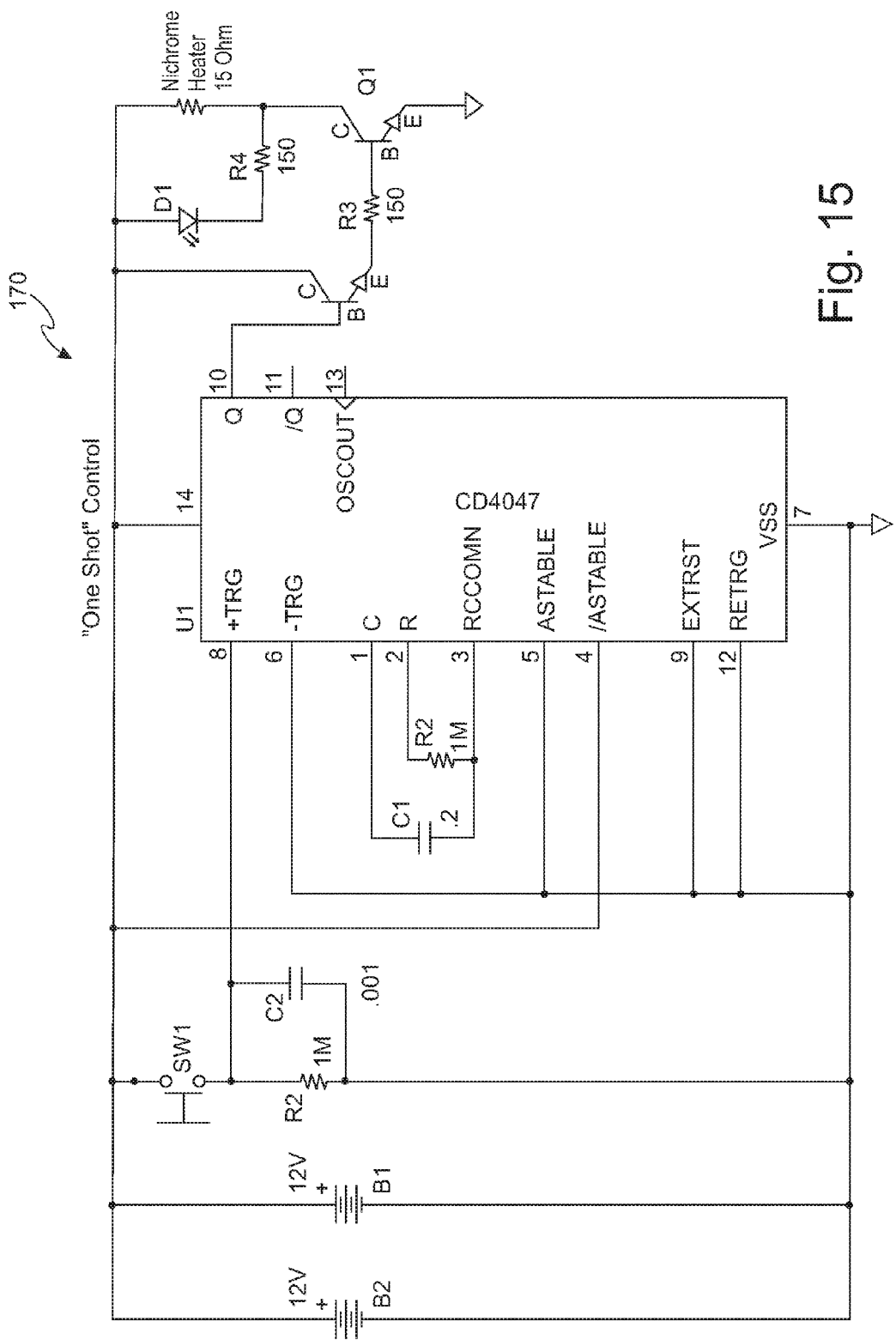
FIG. 15 is a schematic diagram of a "one-shot" circuit that may be used in an embodiment of the power control system of the present invention.
Figure 16:
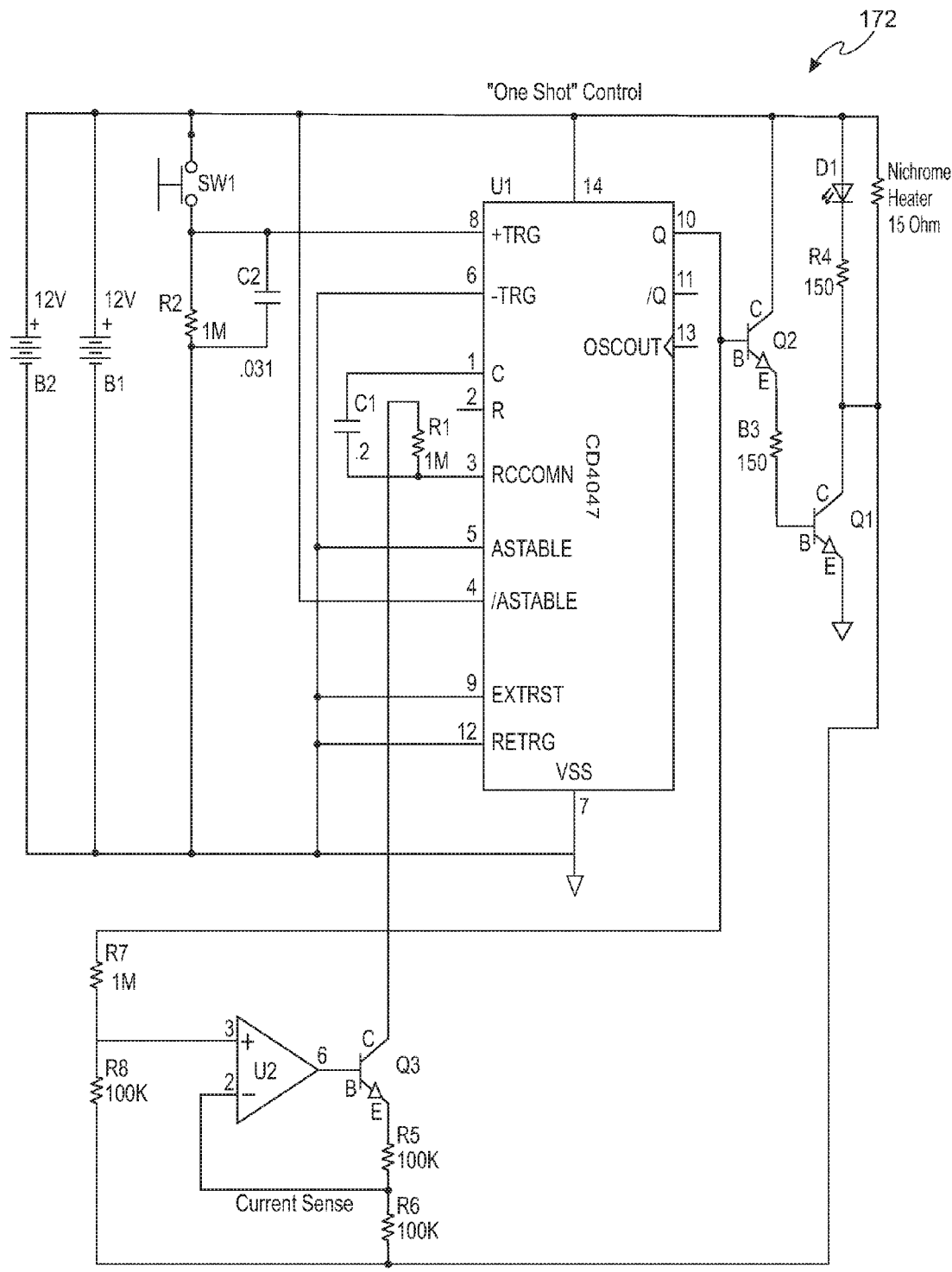
FIG. 16 and FIG. 17 are schematic diagrams of similar modified circuits that may be used in an embodiment of the power control system.
Figure 17:
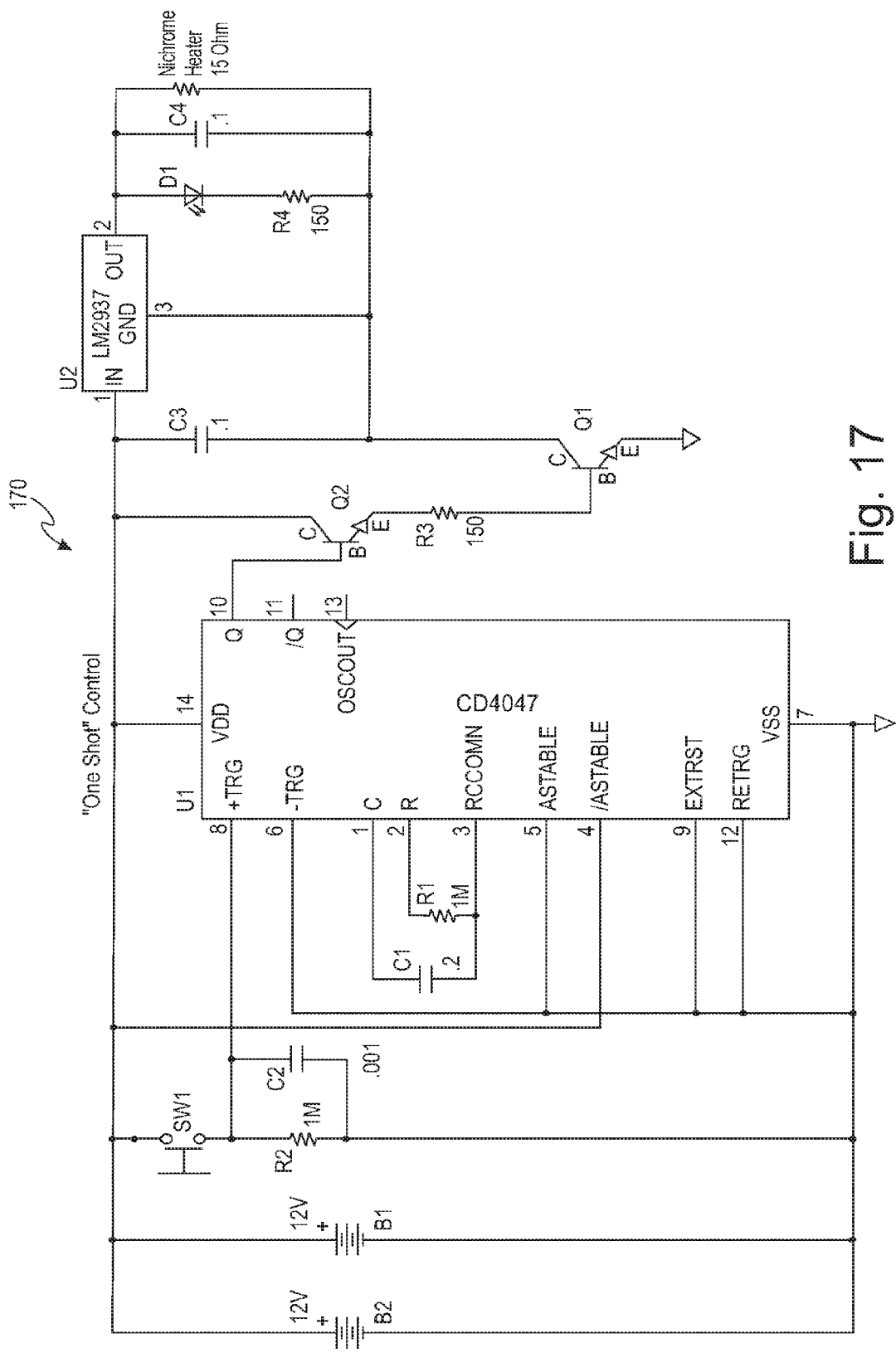

The energy required to completely vaporize a predetermined volume of liquid is a function of the amount of power and the duration of time the power is present. Therefore, the power control system 306 may also comprise a means for controlling a precise duration of time to supply the precise amount of power to completely vaporize the predetermined volume of liquid at the required temperature. The means for controlling a precise duration of time to supply the power may comprise a "one-shot" control circuitry 170, 172, or 174 that can be integrated with the circuit for controlling the amount of power described above. Examples of "one-shot" circuits 170, 172, or 174 are shown in FIGS. 15-17 and described below in more detail. A "one-shot" circuit ay be used to limit the electric current delivery time interval regardless of how long the user holds the lever down. The power control system 306 is completely "off" in between uses; therefore, there is no drain on the battery during idle time. As a result, battery life is prolonged.

In some embodiments, the integrated circuit may be configured to actuate the power source a predetermined number of times. This number should be low enough such that each actuation results in the same amount of power each time. In some embodiments, the integrated circuit may be configured to monitor the battery life and not actuate the power when a predetermined amount of battery life has been detected.

This power control system 306 can be implemented in existing vapor delivery devices. For example, the control system 306 can be installed into handles of current vapor delivery devices to be implemented with existing heating systems to improve the energy efficiency and accuracy of dosing of current devices.

Besides, or in addition to, controlling the amount and duration of the power to significantly prove the efficiency and effectiveness of metering precise doses from vaporization devices, a means for consistently metering a precise volume of a liquid to be vaporized can be used as an alternative or additional layer of precision. Therefore, an efficient medicant delivery device relay comprise a power control system 34 utilizing various embodiments of the circuitry described above to control the efficient and effective use of power, and/or a fluid delivery system 30, 302, or 402 as a means for consistently metering a precise volume of a liquid from the fluid reservoir to precisely control the volume of the liquid discharged for vaporization. Various combinations of these systems may be used to achieve the desired level of accuracy. An atomization or vaporization system 32 may also be required to vaporize the medicant. In this application, atomization and vaporization are referred to interchangeably to indicate that the state of the medicant is a form that can be inhaled and absorbed by the lungs.

The precise volume of liquid that can be completely vaporized at a given temperature and duration of exposure can be calculated. Therefore, the precise volume required to be discharged from a fluid delivery system may be predetermined because the temperature of the wire and the duration the wire is energized can be fixed. Alternatively, in some embodiment, the precise volume may vary depending on the temperature of the wire and how long the remains energized at that temperature.

The embodiments of the power control system described above offer an advantageous way for more precisely metering a specific dose of a medicant. Controlling the volume of the medicant discharged also improves the metering accuracy. Examples of devices for controlling the volume of medicants to a heating element for vaporization are described below. These devices can be used alone or in combination with the power control system to further improve the accuracy of metered doses of medicants.

Figure 5:
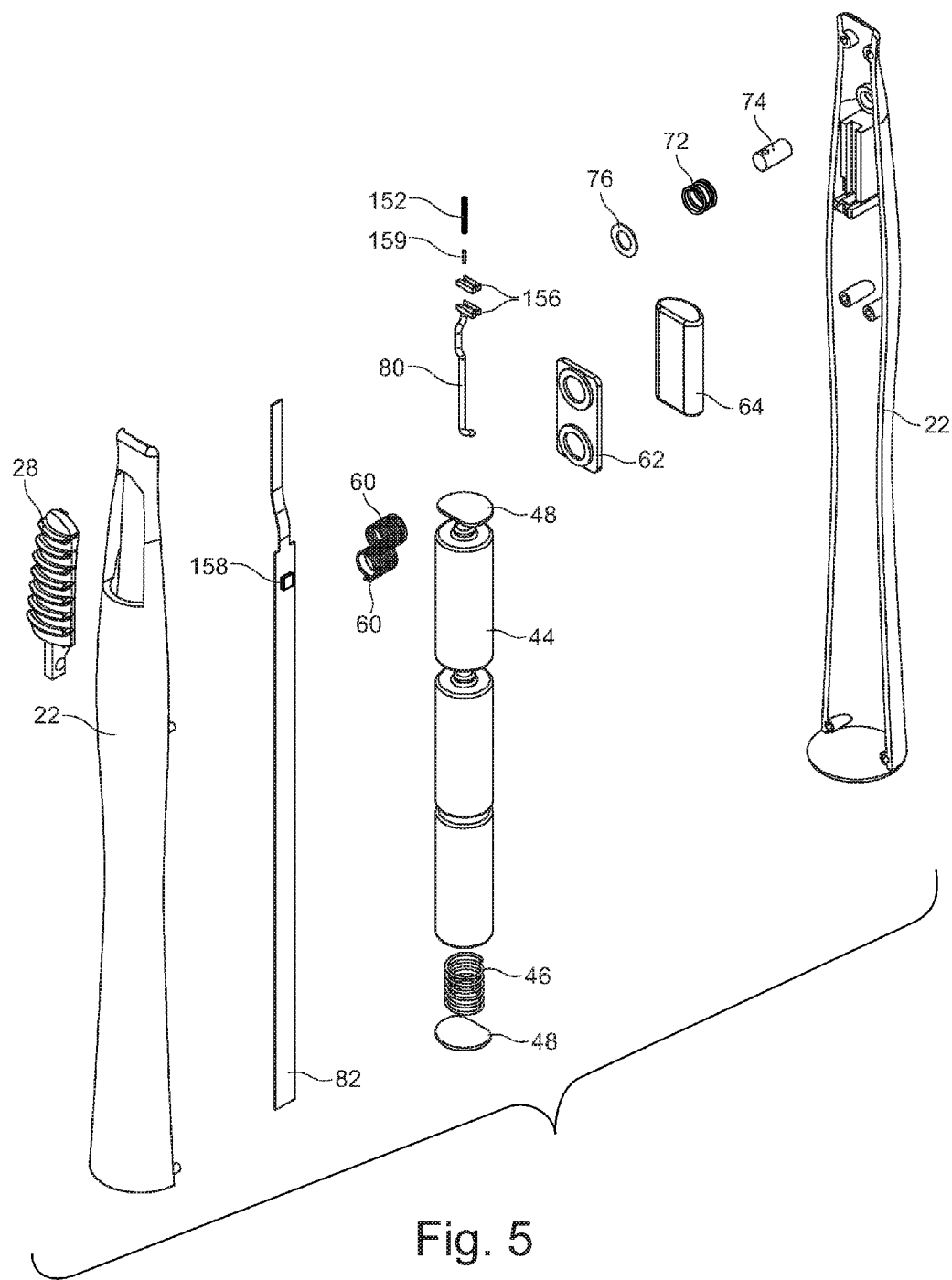
FIG. 5 is an exploded perspective view of the device shown in FIGS. 1-4.

In one embodiment, as shown in FIGS. 1 and 2, a medicant delivery device 20 has an elongated housing 22 with a mouthpiece 24 and a lever 28 adjacent to a back or top end of the housing. A mouthpiece opening 26 extends into the mouthpiece 24. Referring further to FIGS. 3-5, an embodiment of the device 20 includes a fluid or liquid delivery system 30 as the means for consistently metering a precise volume of a liquid to precisely control the volume of the liquid discharged for vaporization, and a vaporizing system 32, as well as an electrical power control system 34. The electrical power control system 34 may include batteries 44 within a battery compartment 42 of the housing 22, and with the batteries electrically connected to a flexible circuit board 82 via a spring 46 and contacts 48. As shown in FIG. 5, the housing may be provided with left and right sides, in a clamshell design. The lever 28 may be attached to the housing 22 at a pivot 58.

As shown in FIG. 4, a means for consistently metering a precise volume of a liquid from a fluid reservoir to precisely control the volume of the liquid discharged for vaporization is achieved by the liquid delivery system 30, in the example shown, which includes a resilient or flex wall liquid chamber or reservoir 64 connected via a tube 66 to a lever valve 70. The reservoir 64 may be a thin walled flexible pouch made of polyethylene film. The reservoir 64 is positioned between two rigid surfaces, with a plate 62 on one side and an inner wall of the housing 22 on the other side. Springs 60 within the housing 22 press on a plate 62, which in turn presses on the reservoir 64. This pressurizes the liquid in the reservoir.

Figure 6:
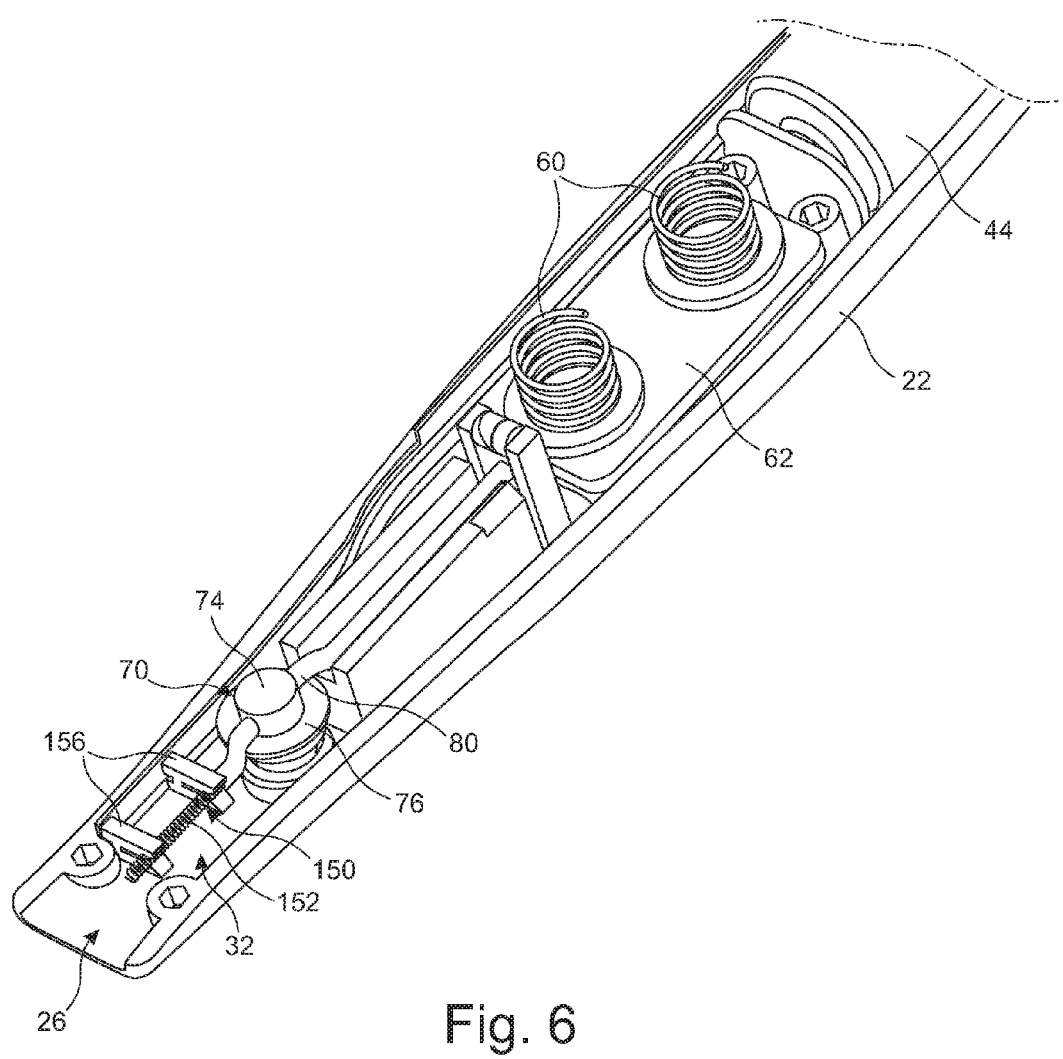
FIG. 6 is an enlarge perspective view of elements of the device shown in FIGS. 3-5.
Figure 7:
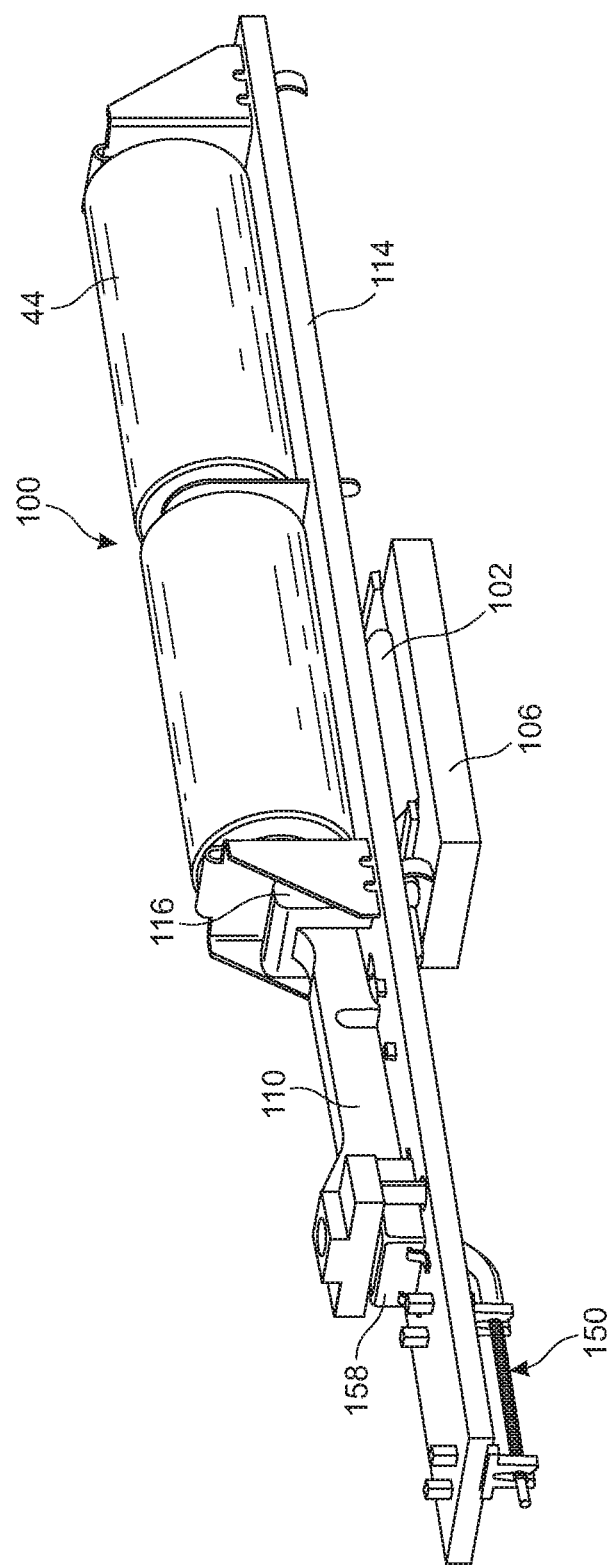
FIG. 7 is a perspective view of another embodiment of the present invention with the housing removed for purpose of illustration.

A tube 66 extends from the reservoir 64 to a lever valve 70 which may include a valve post 74, a valve spring 72 and valve washer 76. A valve section 80 of the tube 66 in this design extends through an opening the valve post 74, as shown in FIG. 6. The valve spring 72 urges the valve washer 76 against the valve section 80 of the tube pinching it closed.

Figure 14:
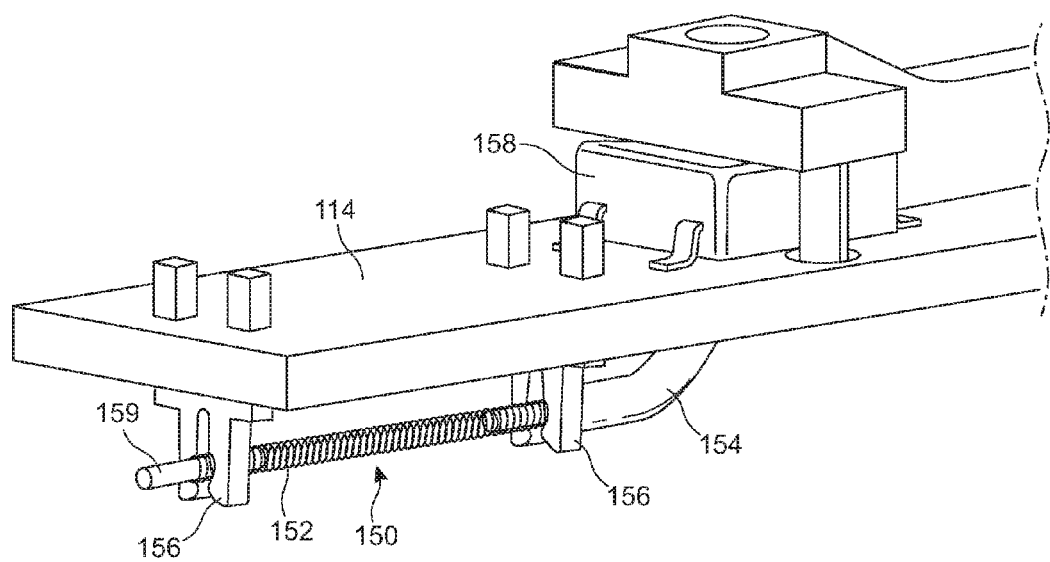
FIG. 14 is an enlarged perspective view of the vaporizing system shown in FIGS. 7-9.

Referring to FIGS. 4-6, an embodiment of the vaporizing system 32 includes a heater 150 which is electrically connected to the electrical power control system 34. The vaporizing system 32 is also connected to, and receives liquid from, the liquid delivery system 30. The heater 150 may be an electrical resistance heater ed by an open coil of wire 152, such as ni-chrome wire. In this design, the electric current is supplied to the coil wire 152 via connectors 156 on, or linked to, the flexible circuit board 82, which in turn in connected to the batteries 44. FIG. 14 shows the connectors 156 for providing electrical power to the heating element.

An outlet segment 154 of the tube 66 extending out of the lever valve 70 towards the mouthpiece or back end of the device is inserted into the front end of a wire coil 152. Referring momentarily to FIG. 14, solid wire inserts 159 may be inserted into the ends of the wire coil 152 and the outlet segment 154 to provide internal support, so that they do not distort or collapse when pressed down into connectors 156. The outlet segment 154 at the front end of wire coil heater 152 provides liquid into the bore of coil with each actuation of the device 20.

The tube 66 is connected to the reservoir 64 with a liquid-tight connection so that liquid can only flow from the reservoir only through tube 66. The tube 66 may be a resilient, flexible material such that its inner lumen can in be completely flattened when compressed, and then generally fully recover to its original shape when released. A lever segment 67 of the tube 66 is positioned beneath the lever 28 and a fixed rigid surface inside of the housing, which optionally may be part of the circuit board 82 on which power management circuitry is located. Locating features 112 may be provided in, on, or through the circuit board 82 to ensure desired positioning is maintained. The lever 28 is retained by lever pivot 116 and can pivot through a controlled range of motion.

In use, the mouthpiece 24 is placed into the mouth and the user presses or squeezes the lever 28. The tube 66 is pre-filled or primed with liquid during manufacture. Referring to FIG. 4, as the lever 28 pivots down about the pivot 58, a pincher 86 pinches the lever segment 67 of the tube 66 against an inside surface of the housing 20, adjacent to the pivot 58 and the reservoir 64. This temporarily closes off the tube 66 at the pincher 86. As the lever 28 continues to pivot down (or inward towards the centerline of the device) a ramp surface 88 of the lever 28 progressively squeezes the lever segment 67 of the tube 66 between the pincher 86 and the lever valve 70. This creates a squeegee type of movement which pumps liquid towards the lever valve 70 using a peristaltic action. As the lever 28 continues to pivot inwardly, posts on the lever press the valve washer 76 down against the force of the valve spring 72. This temporarily opens the lever valve 70 by allowing the valve section 80 of the tube 66 to open. With the valve section 80 of the tube open, and with liquid in the tube being pumped via the ramp surface 88, a bolus of liquid flows through the valve section 80 and the outlet segment 154 and into the wire coil 152.

The constant positive pressure exerted on the reservoir 64 by the springs 60 pressurizes the liquid in the tube 66. However, since the tube 66 is pinched closed by the pincher 86, no liquid flows out of the reservoir when the lever is depressed and the lever valve is opening. Rather, the liquid already present in the tube 66 between the pincher 86 and the lever valve 70 provides the measured bolus which is uniformly delivered to the wire coil.

The downward movement of the lever 28 also closes a switch 158 linked to or located on the circuit board 82. Electric current then flows from the batteries 44, or other power source, to the wire coil 152. The wire coil heats up causing the liquid to vaporize. The current supplied to the wire coil, and the temperature of the wire coil when operating, may be regulated by the circuit board, depending on the liquid used, the desired dose, and other factors. The switch 158 may be positioned to close only when the lever 28 is fully depressed. This avoids inadvertently heating the wire coil. It also delays heating the wire coil until the bolus of liquid is moved into the wire coil via the pivoting movement of the lever, to help prolong battery life. A "one-shot" control circuit 170, for example, as shown in FIG. 15 described below, may be used to limit the electric current delivery time interval regardless of how long the user holds the lever down. The power is completely "off" in between uses. There is no drain on the battery during idle time. As a result, battery life is prolonged.

As is apparent from this description, the liquid delivery system 30, using a linear peristaltic pumping action, delivers a consistent, fixed, repeatable bolus of liquid to vaporizing system 32 with each actuation of the device 20. The liquid delivery system 30 further seals the reservoir 64 between actuations via the pincher 86, maintains the contents of the reservoir in a pressurized state, and controls electric power delivery to the vaporizing system 32. The liquid delivery system is designed so that as liquid is used, air is not introduced into the system.

The diameter and length of the wire coil 152 forms a cylindrical volume within the inside diameter of the coil that is sufficient to capture a single expressed dose of liquid from the liquid delivery system. The adjacent loops of wire of the wire coil 152 may also be positioned so that liquid surface tension holds the liquid within the bore of the coil. This allows the device 20 to be used in any orientation, since gravity is not needed to keep the released dose of liquid in place.

The use of an open coil offers the further advantage that the vapor may be generated and escape anywhere along the length of the coil, without inadvertently affecting vaporization of the balance of the bolus of liquid in the coil. The wire coil also provides a large surface area for heat transfer and minimizes energy loss resulting from heating ancillary components.

Upon application of electric power, liquid in the coil vaporizes and passes through gaps between coils. The coil can be sized and shaped and positioned in the housing so that the vapor generated can be entrained into an air stream drawn through the device 20 when the user inhales on the mouthpiece. "Inhale" here means drawing the vapor at least into the mouth.

FIGS. 7-13 show a second device embodiment 100 which may be similar to the device 20, but with the following differences. In the device 100, the means for consistently metering a precise volume of a liquid from the fluid reservoir to precisely control the volume of the liquid discharged for vaporization comprises a foam pad 106 that is compressed and inserted between a reservoir 64 and one of the rigid walls of the housing. Force exerted on the reservoir 64 by the foam trying to recover to its relaxed state exerts compressive force on the reservoir which maintains the liquid in the reservoir under pressure. The foam pad 106 may be used in place of the springs 60 shown in FIG. 4. The reservoir may alternatively be pressurized using a syringe with a spring-biased plunger. With any of these designs, the reservoir may optionally be provided as a replaceable cartridge.

Figure 8:
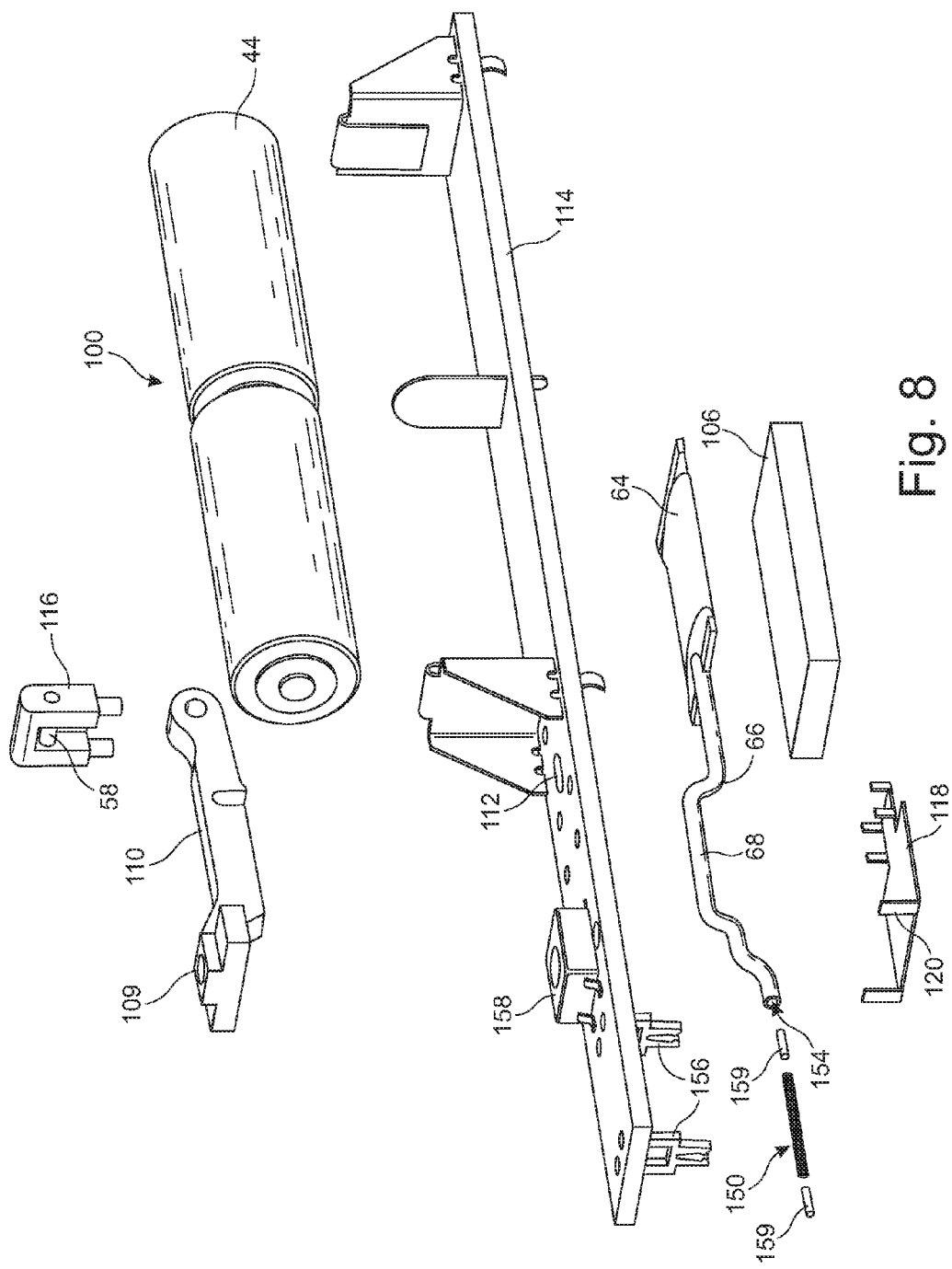
FIG. 8 is an exploded perspective view of the embodiment shown in FIG. 7.
Figure 9:
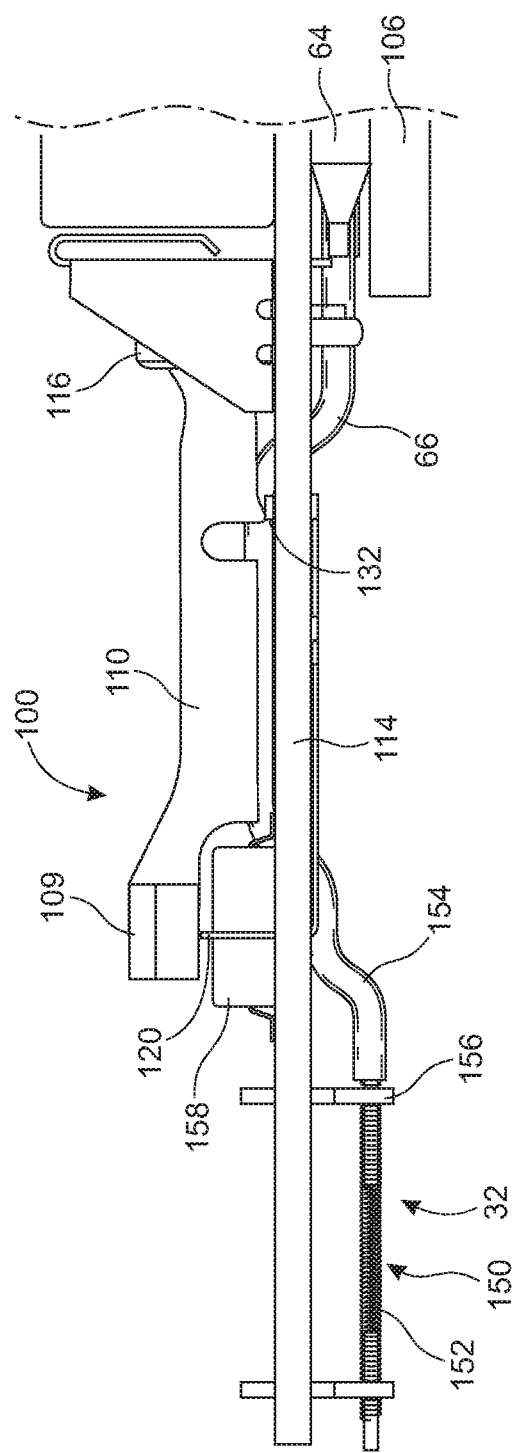
FIG. 9 is an enlarged side view showing details of elements shown in FIGS. 7 and 8.

As shown in FIG. 8, in the device 100, a lever valve 118 is provided (in place of the pincher 86 in the device 20) to compress the front end of the tube 66, preventing liquid from flowing out from the pressurized reservoir in between uses. The lever valve 118 may be a stamped sheet metal form soldered to a rigid circuit board 114 containing the same or similar circuitry as described above for the power control system 34.

FIGS. 10-13 show additional features that can be used for a means for consistently metering a precise volume of a liquid from the fluid reservoir to precisely control the volume of the liquid discharged for vaporization, specifically, the pumping action of the liquid delivery system in the device 100. When a dose of vapor is desired, the user places the mouthpiece in the mouth and inhales while pressing a button 109 on the lever 110, causing the lever to rotate downward (counter-clockwise). As the lever 110 initially rotates as shown in FIG. 10, a lever pinch projection 132 clamps or pinches the tube 66 closed at a pinch point 140, closing off the pressurized liquid reservoir. Continued rotation of lever 110 causes the lever 110 to flex at a flex point 124 having reduced thickness, as shown in FIG. 11. This allows over-travel rotation of the lever while the tube 66 remains closed off at the pinch point 140, without crushing the tube.

Further rotation of lever 110 then compresses the lumen of the pump segment 68 of the tube 66. This pumps liquid from the pump segment 68 towards the lever valve 118. This movement also moves projections on the lever which push valve flanges 120 down, deflecting and opening the lever valve 118, and allowing a pressurized bolus of liquid to move through the tube and into the vaporizing system 32. The dotted lines in FIG. 12 show the lever valve 118 deflected down and away from the bottom surface of the circuit board 114, to open the valve. Lastly, at end of the lever stroke, a lever switch protrusion contacts a switch 158, switching the power delivery system on.

When lever 110 is released, it pivots back up to its original position. As the lever returns, the lever valve 118 reseats first, sealing the back end of pump segment 68 of the tube 66 and preventing air from being drawn back into the pump segment. As the lever 110 continues to rotate clockwise, the pump segment 68 decompresses, creating a negative pressure within the tube lumen. Lastly, at pinch point 140 the tube 66 reopens, allowing pressurized liquid from the reservoir to enter, refilling pump segment 68 with liquid to provide the next dose.

The volume of liquid expressed with each stroke can be controlled by selection of desired pump segment 68 tube diameter and length. Maintenance of a positive pressure on the liquid reservoir ensures that the system always stays primed with liquid, and that "short shots" resulting from air bubbles in the tube do not occur. Furthermore, sealing of the vaporizer system with a valve such as the valve 70 or 118 that is only actuated at the time of delivery, and positive pressure dispensing prevents inadvertent leakage of liquid irrespective of orientation of the device during storage or use, thereby providing a means for consistently metering a precise volume of a liquid from the fluid reservoir to precisely control the volume of the liquid discharged for vaporization.

FIG. 15 is a schematic diagram for a "one-shot" circuit 170 for the power control system that delivers a fixed time interval of electric current to the heater 150 regardless of how long the lever is depressed by the user. In FIG. 15, CD4047 is a CMOS low power monostable/astable multivibrator available for example from Texas Instruments. U1 is a common CD4047 which operates from a 12V battery voltage with very low quiescent current drain. When pushbutton SW1 is depressed, U1 is triggered, Q (pin 10) goes high and C1 is rapidly charged to near the supply voltage through a FET within U1. At the same time, resistor R1 is switched to a logical "0" state and immediately begins discharging capacitor C1 with the time constant of 1/RC.

A wide range of pulse durations may be selected. Using a typical ni-chrome wire coil, pulse durations ranging from approximately 0.2 to 2 seconds are sufficient to fully vaporize the bolus of liquid. When the voltage on pin 3 reaches the threshold for logic "0" (~⅓ supply voltage), the logic levels switch and Q (pin 10) returns to a logic low level. Q2 is an emitter follower that provides current amplification to enable Q1 to be fully saturated during the desired current pulse. D1 and R4 provide a visual indication of the heater current. R2 is a "pull down" resistor for SW1, and C2 prevents induced noise from falsely triggering the circuit. Other choices of IC may be employed, such as the Toshiba TC7WH123, depending upon battery voltage, package size, and cost.

The battery voltage gradually decreases over the lifespan of the device. For many applications, the circuit described in FIG. 15 provides the necessary control. Ho ever, more precise metering of the medicant may be accomplished by increasing the current pulse duration as the current decreases over the discharge life of the battery. In the circuit 172 shown in FIG. 16, an additional OP amp IC serves as a voltage controlled current source for the power control system. The input voltage is sampled from Pin 10 of U1. A constant current is generated in Q3 and used to discharge the timing capacitor, C1, at a constant rate. Once the voltage across C1 reaches the logic threshold, CD 4047 trips and the output pulse width is complete. As the battery voltage decreases the constant current generated in Q3 decreases, causing the time to discharge C1 to increase. This lengthens the output pulse to maintain a relatively constant heater power per inhalation cycle as the battery voltage declines over the lifetime of the device. The various current setting and sense resistor values may be adjusted to provide optimal performance. Other circuits may be employed to provide the same function such as voltage to frequency converters.

FIG. 17 shows another circuit 174 for the power control system where a voltage regulator U2 is inserted between the output transistor Q1 and the heater filament. This keeps the filament voltage constant throughout the battery life. The regulated voltage may be chosen to optimize the heater operation near end of life. A low dropout regulator is desired to maximize the lifespan before regulation is no longer maintained. A simple linear regulator is shown, but a high efficiency, switching regulator may also be employed to improve efficiency. The pulse duration is maintained as described above or an equivalent "one shot" circuit and the heater current is kept constant by the voltage regulator.

In another alternative design, the electrical power control system 34 may be configured to provide consistent power by timing the power to provide the minimum energy needed to vaporize the liquid. The power control system 34 may also be programmed to do this. For example, the electrical power control system 34 may be programmed to power the source down to the voltage required to vaporize the liquid, so as to extend its useful life. Here, the power source may include a capacitor that builds, retains and provides a charge necessary to vaporize the liquid to be vaporized, again, so as to extend the useful life of the power source. In some embodiments, supercapacitors may be employed as discussed above to further enhance the functionality of the power source.

Figure 18:
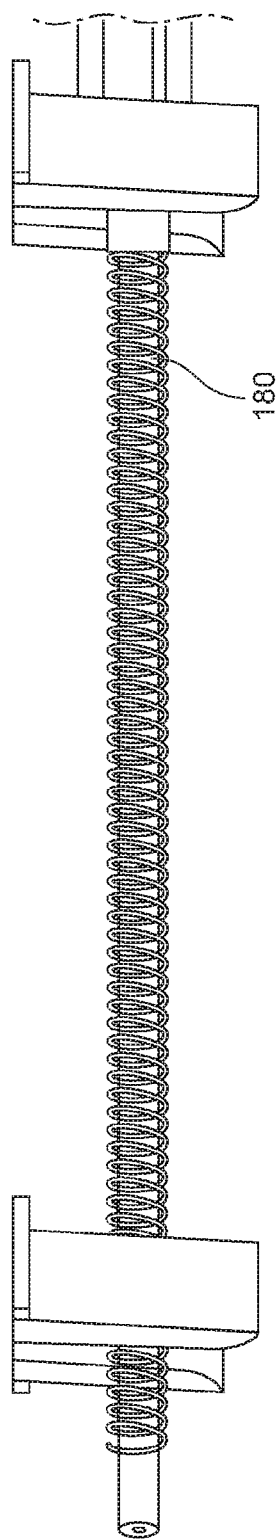
FIG. 18 is an enlarged side view of an embodiment of a vaporizing element.

In an additional alternative design shown in FIG. 18, the liquid to be atomized is delivered into a small diameter tube 180 via capillary action, as distinct from providing the liquid via pressure into the heating coil, where it is stabilized for vaporization due to surface tension. The tube 180 can be glass, polyaniline or metal, e.g., stainless steel. A heating element such as ni-chrome wire can be coiled around the tube, coiled into the tube or inserted into a tube in a V-shape so as to heat the entire volume of liquid at the same time.

Figure 19:
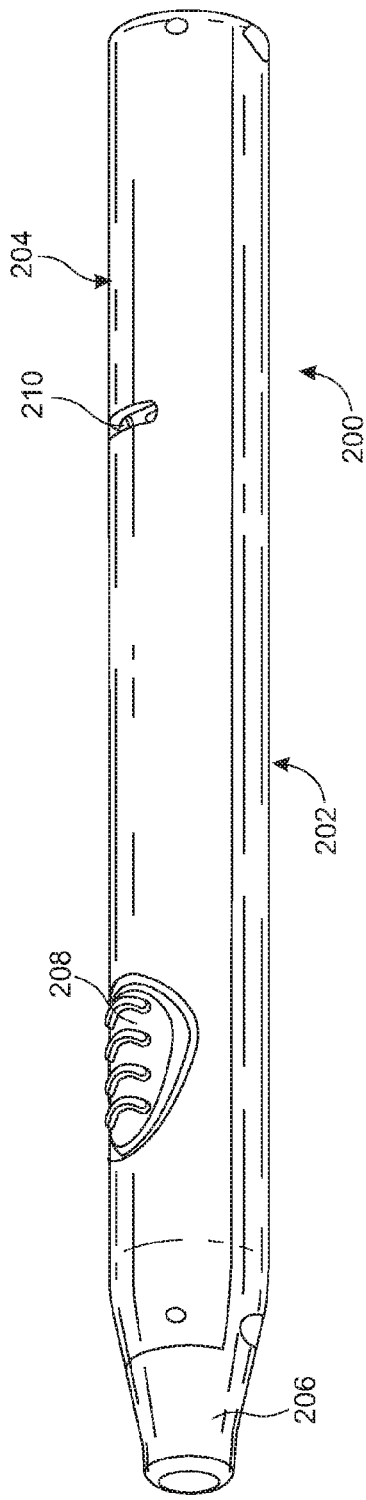
FIG. 19 is a perspective view of another embodiment of the vaporizing device
Figure 20:
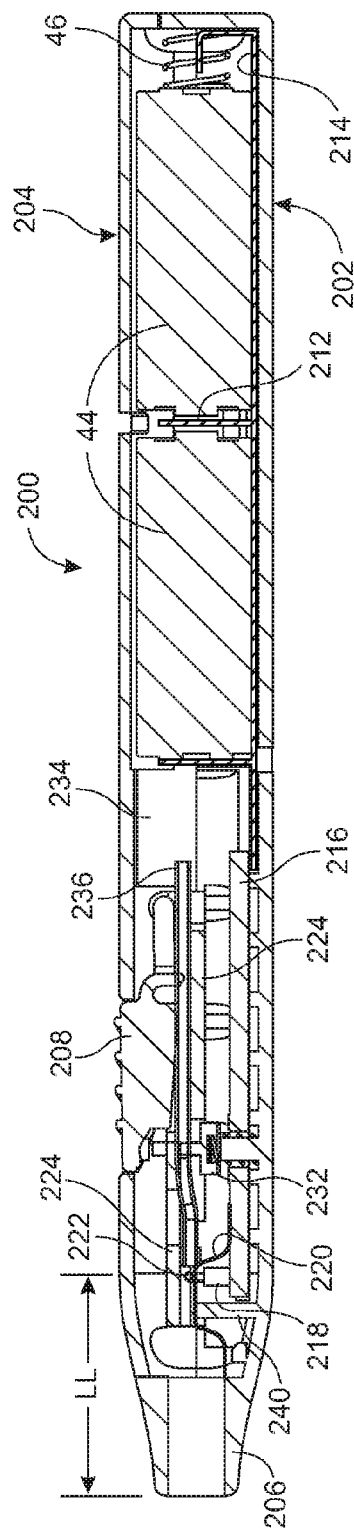
FIG. 20 is a section view of the vaporizing device shown in FIG. 19.
Figure 21:
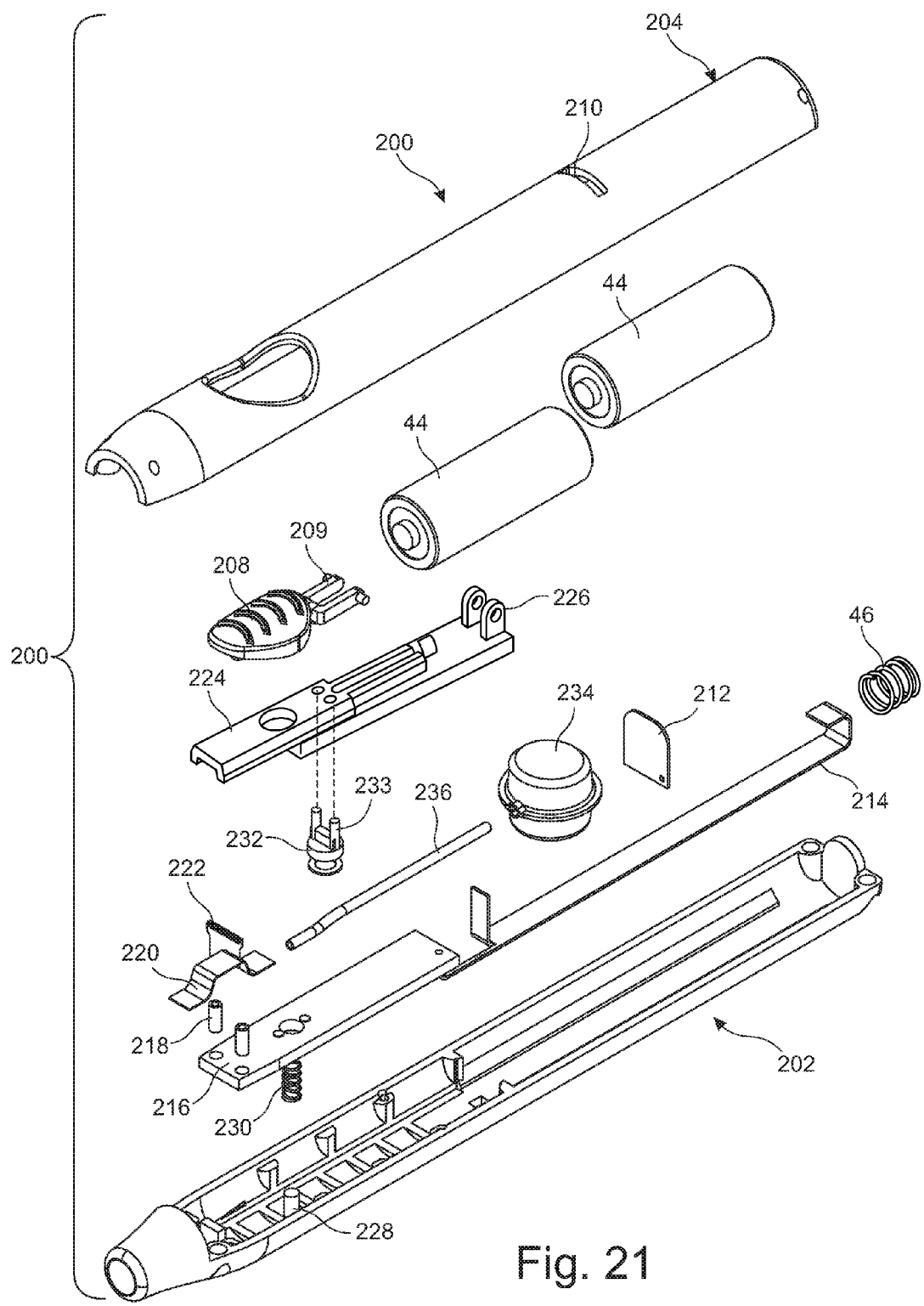
FIG. 21 is an exploded perspective view of the vaporizing device shown in FIGS. 19 and 20.

FIGS. 19-22 show an alternative vaporizing device 200 having a housing formed from a base 202 including a mouthpiece 206, and a cover 204 attached to the base 202. Pivot arms 209 on a button 208 are pivotally attached to pivot posts 226 on a bridge 224, as shown in FIG. 21 to provide another means for consistently metering a precise volume of a liquid from the fluid reservoir 234 to precisely control the volume of the liquid discharged for vaporization. The radius 244 of the pincher 238 can flex when the tube 236 is compressed. The bridge 224 has pins for securely attaching it to the base 202. The positive electrode of each battery 44 is held into contact with center contact 212 by a spring 46. A positive conductor strip 214 connects the center contact to a printed circuit board 216.

Figure 22:
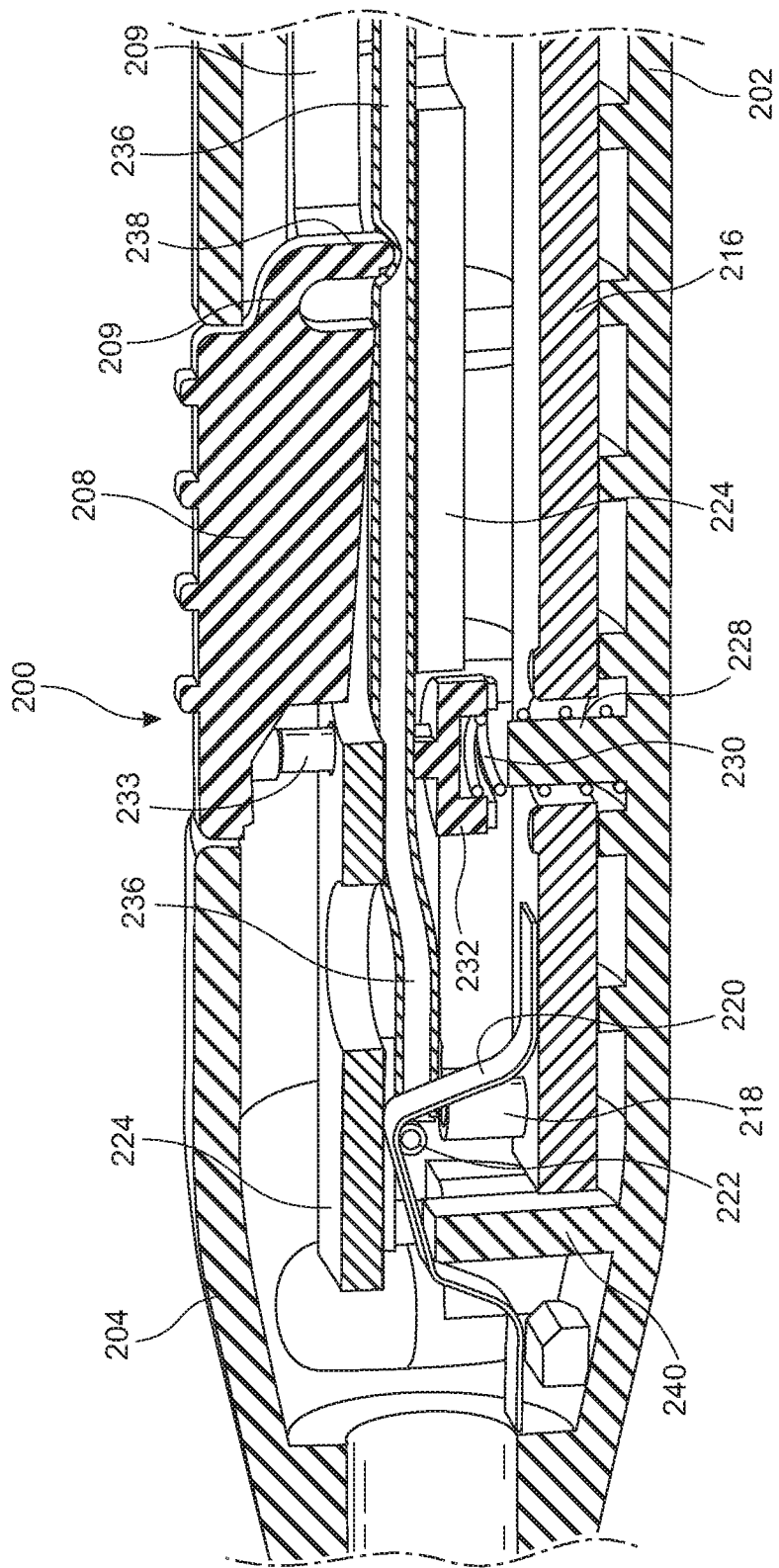
FIG. 22 is an enlarged perspective view of elements shown in FIG. 20.

Referring to FIG. 22, a wick 220 extends from the printed circuit board 216 (containing the same or similar circuitry as described above for the power control system 34) up to a vaporizing coil 222 and optionally over a raised wall 240. The wick may be a strip or sheet of ceramic tape 220 that serves as a wick and a heat sink. The wick 220 is positioned between the heating element, such as the vaporizing coil 222, and the outlet of the tube 236. The wick 200 may rest on top of the heating element, or be positioned adjacent to it, and the tube outlet may also be on top of the heating element and the wick 220 (when the device 200 is in the upright position, with the button 208 on top).

Brass posts 218 or similar contacts are attached to the printed circuit board 216 and to opposite ends of the coil 222. The button 208 has a pincher arm 209 positioned to pinch and close off flow in a tube 236 connecting a liquid reservoir to an outlet location on, adjacent to or overlying the wick 220. The tube 236 may be held in place by molded in tube clips 240 on the bridge 224. Arms 233 on ally closed pinch valve 232 extend up through openings in the bridge 224. A valve spring 230 around a post 228 holds the valve 232 into the normally closed position. A bottom surface of the valve 232 may act as a switch with the printed circuit board 216, or actuate a separate switch on the printed circuit board 216 to switch on electrical current to the coil 222 when the button 208 is pressed.

In use, the vaporizing device 200 operates on the same principals as described above, with the following additions. A slot 210 may be provided in the housing to accommodate an insulating tab. The insulating tab is installed during manufacture and prevents electrical contact between the center contact 212 and the batteries. As a result, the device cannot be inadvertently turned on during shipping and storage. Battery life is therefore better preserved. Before operating the vaporizing device 200 for the first time, the user pulls the tab out of the slot 210. As shown in FIGS. 19 and 20, the mouthpiece is round. The dimension LL in FIG. 20 between the coil 222 and the mouthpiece tip may be minimized to 15, 10 or 5 mm. The liquid reservoir may have a volume exceeding 0.8 or 1.0 ml to allow foam compression to pressurize the pump. In the device 200, the liquid supplied from the reservoir via the tube 236 is not delivered into the coil 222. Rather the liquid is delivered onto the wick 220. The heating coil 222 abuts the wick 220 and heats the wick, which then vaporizes substantially all of the liquid on or in the wick.

In each of the vaporizing devices described above, the open coil heater 152 or 222 of e.g., ni-chrome wire may be encased in a porous ceramic material, so that the vapor produced when the fluid is atomized must pass through the ceramic material in order to be ingested or inhaled. The ceramic material can be manufactured with techniques that control the size of the pores through which the vapor will pass. This can help to regulate the size of the vapor molecules or droplets produced for inhalation. By controlling the amount of electrical power and the duration of power to the coil heater, the heater continues to vaporize the fluid at the heater until the vapor droplets or particles are small enough to pass through the ceramic al, effectively utilizing all the fluid delivered to the coil and controlling the dose in addition to regulating the molecule size. By regulating the size of the vapor molecule produced, the vaporizing devices can be used with snore precision and with fluids and medicants that require carefully controlled dosages particle sizes. In some cases, smaller molecules may be advantageous as they Lair be inhaled more deeply into the lungs, providing better a snore effective delivery mechanism.

The wire coil heater may alternatively be encased in a heat resistant fabric-like material, such as Kevlar® so that the vapor must pass through the fabric to be ingested. The fabric can be manufactured with a desired mesh opening size, to regulate the size of the vapor particles and/or molecules delivered by the vaporizer. By controlling the amount of electrical power and the duration of power to the heater, the heater continues to vaporize the fluid delivered to the heater until the vapor particles are small enough to pass through the mesh of the fabric. Containing the fluid inside the fabric with the heater until the particles are sufficiently small enough to pass through the fabric can help to effectively atomize and deliver all the fluid delivered to the heater, with little or no waste, in turn controlling the dose.

Although the switch 158 is described above as a mechanical contact switch, other forms of switches may optionally be used, including switches that optically or electrically sense the movement of position of an element, or a switch that senses the presence of liquid in the heater 150. In addition, though the lever and pinch valves are shown as clamping type of valves, other forms of mechanically or electrically operated valves may be used. Similarly, the peristaltic pumping action created by the pivoting movement of the lever may be optionally replaced with alternative forms of pumping or fluid movement. Various types of equivalent heating elements may also be used in place of the wire coils described. For example, solid state heating elements may be used. The heating element may also be replaced by alternative vaporizing elements, such as electro-hydrodynamic or piezo devices that can convert liquid into a vapor without heating.

Figure 23:
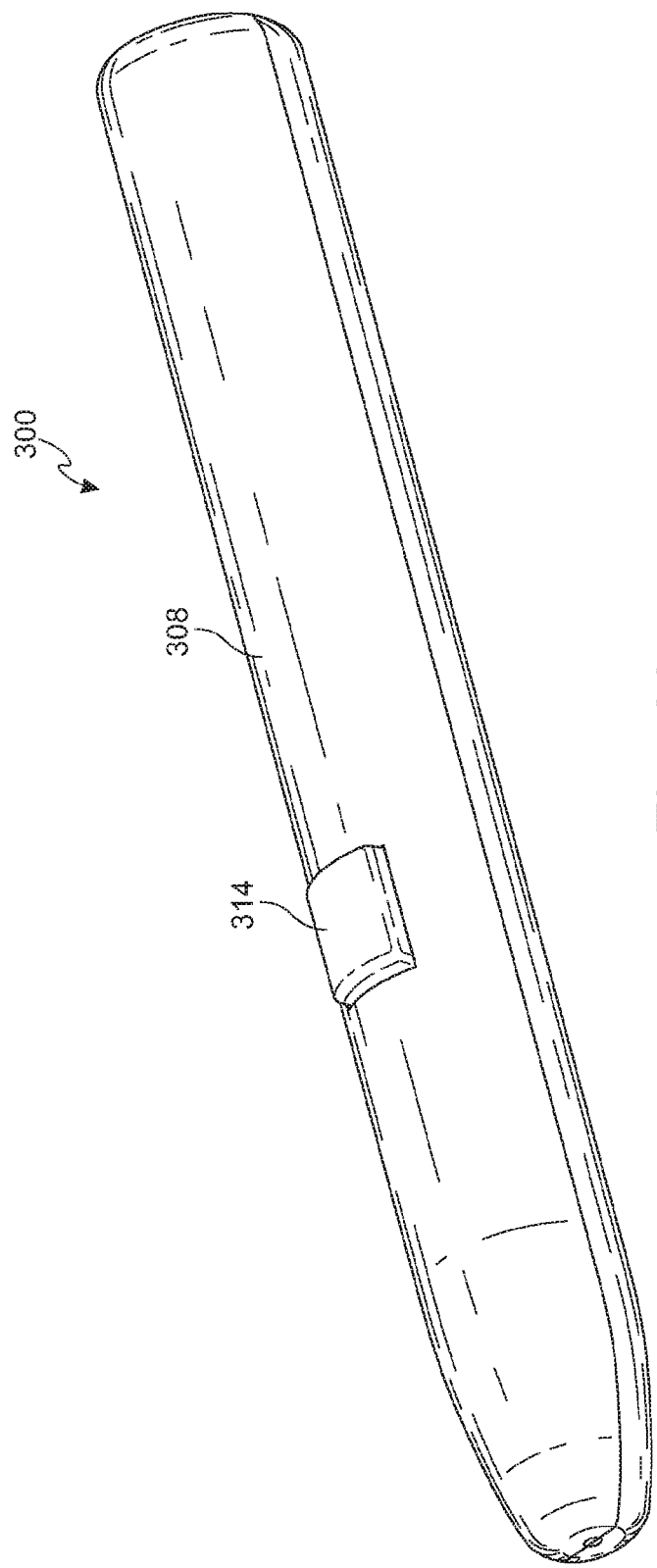
FIG. 23 is an isometric view of another embodiment of the medicant delivery device.
Figure 24:
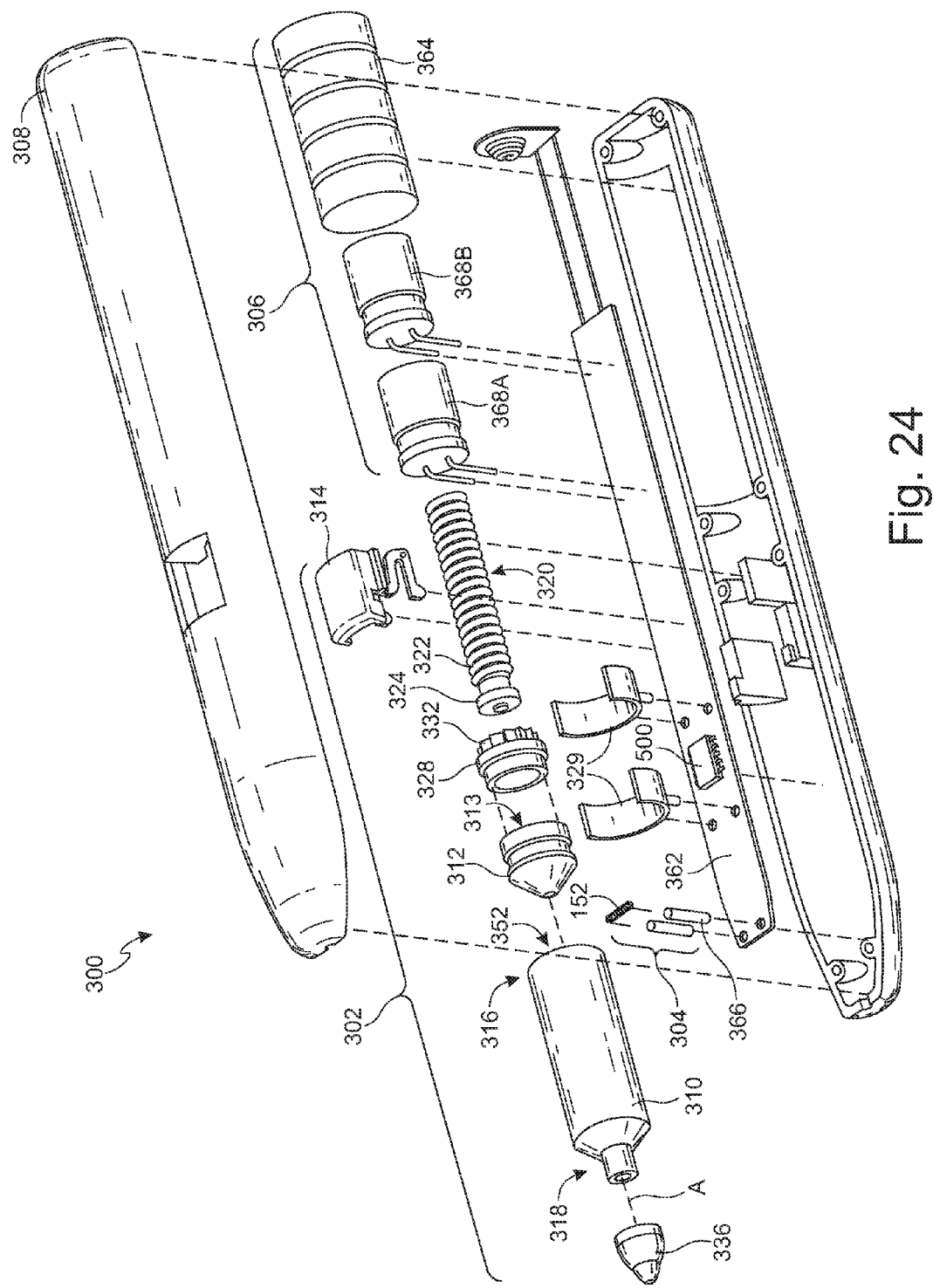
FIG. 24 is an exploded view of the device shown in FIG. 23.
Figure 27:
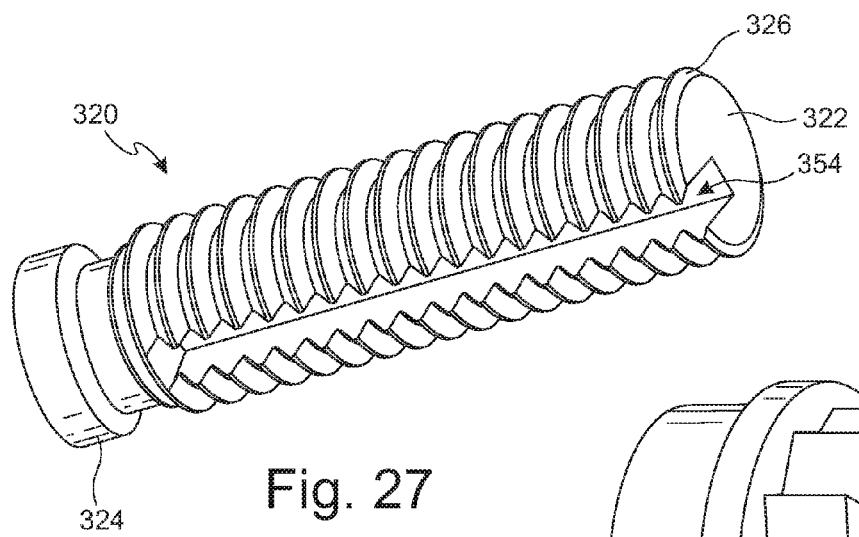
FIG. 27 is a close-up isometric view of an embodiment of a plunger of the fluid delivery system shown in FIG. 28.
Figure 28:
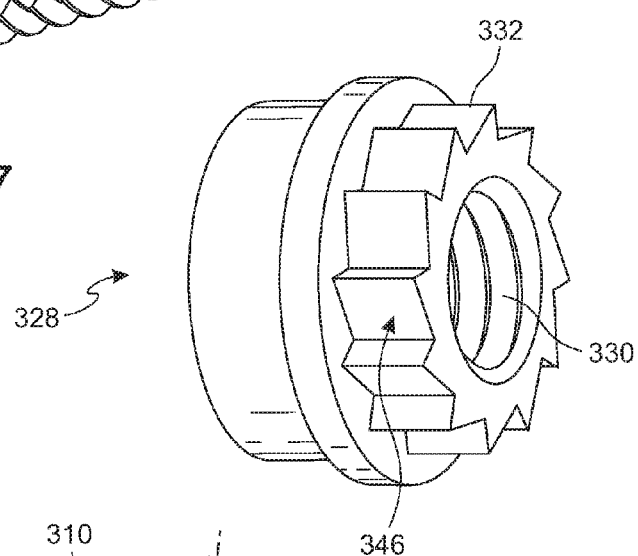
FIG. 28 is a close-up isometric view of an embodiment of a drive nut of the fluid delivery system shown in FIG. 24.
Figure 29:
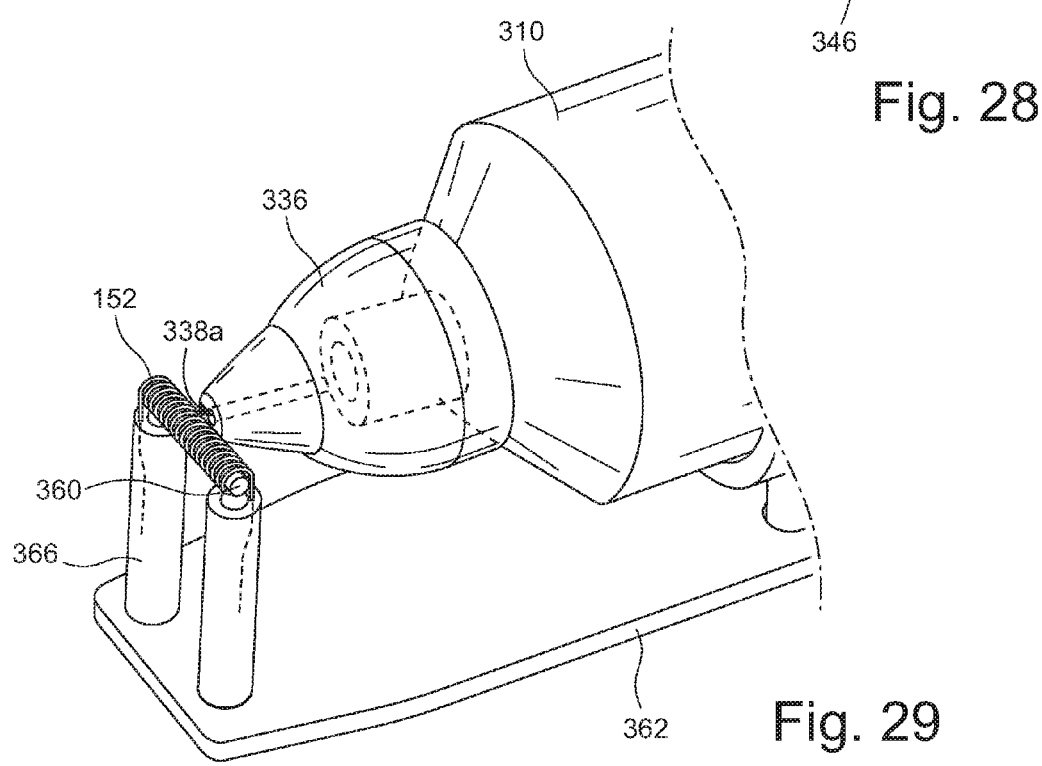
FIG. 29 is a close-up isometric view of an embodiment of the outlet cap and vaporizing system of the medicant delivery device shown in FIG. 24.

In another embodiment, a delivery device 300 utilizes a plunger-style liquid delivery system 302 as another means for consistently metering a precise volume of a liquid from a fluid reservoir to precisely control the volume of the liquid discharged for vaporization. As shown in FIG. 23, the delivery device 300 comprises a new liquid delivery system 302, but utilizes the same or similar an atomization or vaporization system 32 and power control system 34 described above, all contained in a housing 308, preferably cylindrical in shape to mimic a cigarette or cigar.

The fluid delivery system 302 has a fluid reservoir 310 to contain the medicant and a pressure generator, such as a piston 312 that indexes forward inside the fluid reservoir 310 in a consistent, fixed, repeatable amount every time fluid discharge actuator, such as a button 314, is pressed or actuated. Preferably, the fluid reservoir 310 is cylindrical in shape, and more preferably, shaped like a syringe. The delivery device 300 is completely sealed between applications such that the medicant cannot evaporate during storage or between actuation cycles.

The fluid reservoir 310 has a proximal end 316 and a distal end 318. The proximal end 316 is configured to accept the piston 312 which forms a hydraulic seal against the walls of the reservoir 310, such that the medicant cannot leak past the piston 312. The piston 312 may have a hollow core 313. A plunger 320 is provided to couple with the piston 312 to drive the piston 312 forward in a controlled and step-like manner. The plunger 320 comprises a shaft 322 having a head 324 at one end. In a preferred embodiment, the head 324 is flanged. The head 324 is configured to engage with mating geometry on the inside of the piston 312, securing the piston 312 to the plunger 320. The shaft 322 of the plunger is configured with a male screw thread 326, preferably, for its entire length.

A drive nut 328 is disposed at the proximal end 316 of the reservoir 310. Various features of the housing 308 and reservoir 310 constrain the position of the drive nut 328 such that it is free to move rotationally concurrent to the axis A of the plunger 320, but prevent translation in any other direction. The drive nut 328 has a mating female screw thread 330 to the plunger 320 and is threaded onto the plunger 320. The drive nut 328 is further configured with ratchet teeth 332, which interact with a pawl 334 on a button 314 described later such that during operation, the drive nut 328 will rotate in a single direction.

A cap 336 is disposed at the distal end 318 of reservoir 310. The cap 336 may be an elastomeric component with an outlet 338 comprising a self-collapsing slit/hole. Preferably, the cap 336 is made of silicone. The outlet 338 is responsive to pressure from the medicant within the reservoir 310 such that when the medicant is at a higher pressure than the ambient pressure outside of the reservoir 310, the outlet 338 will open 338A, allowing medicant to escape the reservoir 310. Once enough medicant has escaped the reservoir 310 to equilibrate with ambient pressure, the outlet 338 will automatically collapse, sealing the remaining contents of the reservoir 310 from ambient, thereby, preventing loss of medicant to evaporation. So, the measured dose is determined by proper calibration of the pressure needed to properly form and maintain a droplet of the medicant at the outlet 338 until vaporization is initiated. The nature of seal is such that pressure changes external to the device will not cause the reservoir to come "unsealed" the external pressure changes would not be focused enough nor forceful enough to "unseal." And, the natural elasticity of the reservoir would cause the seal to "re-seal" irrespective of external pressure changes.

Based on the surface tension of the liquid medicant, the volume of the medicant discharged from the outlet 338 should be small enough that it forms a droplet at the outlet 338 that adheres to the outlet 338 without dropping or dripping off from the cap 336. The distance from the outlet 338 to the coiled wire 152 should also be small enough that a droplet of the liquid formed at the outlet bridges the gap between the outlet 338 and the coiled wire 152 thereby allowing the droplet to transfer to the coiled wire 152 or the wick 360 within the coiled wire 152. This configuration allows the vapor delivery device 300 to be used in any orientation; thereby, improving the versatility over current devices.

Figure 30:
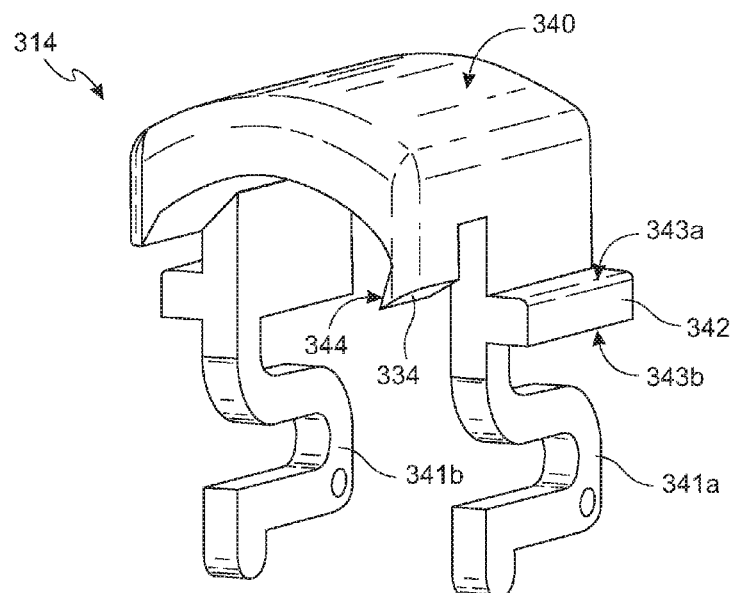
FIG. 30 is a close-up isometric view of an embodiment of a fluid discharge actuator of the medicant delivery device shown in FIG. 24.

As shown in FIG. 30, the button 314 functions to provide controlled rotational indexing of the drive nut 328. The button 314 includes a control surface 340 protruding through the upper housing for the user to actuate the button 314. In its neutral (home) position, the button 314 is normally protruding slightly from the housing 308. The button 314 is constrained such that it can translate in a direction normal to the control surface 340 when it is pressed. The button 314 is configured with two spring elements 341a, 341b which bias the button back to its neutral position in the absence of pressure on the control surface 340. The spring elements 341a, 341b are designed to deform under pressure on the load surface and return to their original shape upon release of that pressure. The range of button travel motion is limited by a stop 342 having an upper surface 343a and a lower surface 343b. The stop surfaces 343a, 343b engage opposing surfaces on lower and upper housings at limits of button travel, creating a fixed range of displacement for the button 314 when it is pressed/released. The button 314 is further configured with a pawl 334 to engage ratchet teeth 332 on the drive nut 328. When the button 314 is depressed, the pawl 334 engages ratchet teeth 332, causing the drive nut 328 to rotate. Upon release, a sloped surface 344 of a pawl 334 and an opposing surface 346 of the ratchet 332 oppose one another, deflecting the pawl 334 at a web allowing the pawl 334 to ride over the adjacent ratchet tooth and the button 314 to return to its neutral position. In this manner, the ratchet 332 allows the drive nut 328 to rotate in a single direction.

Figure 31A:
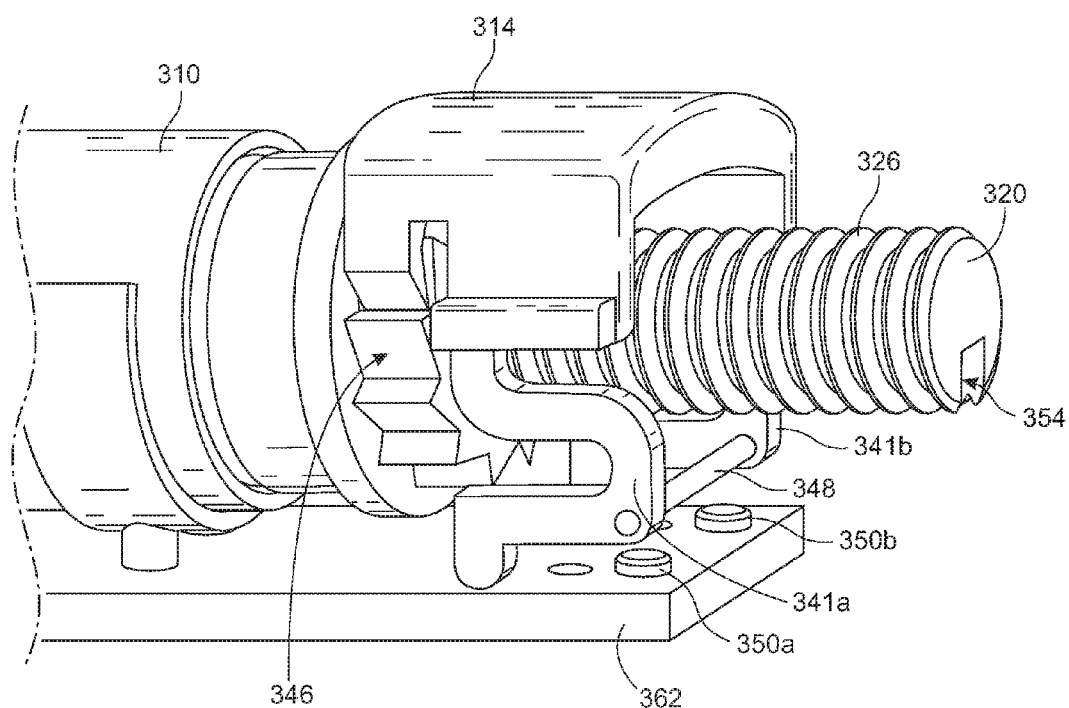
FIG. 31A is a close-up isometric view of a proximal end of the fluid delivery system of the medicant delivery device shown in FIG. 24.
Figure 31B:
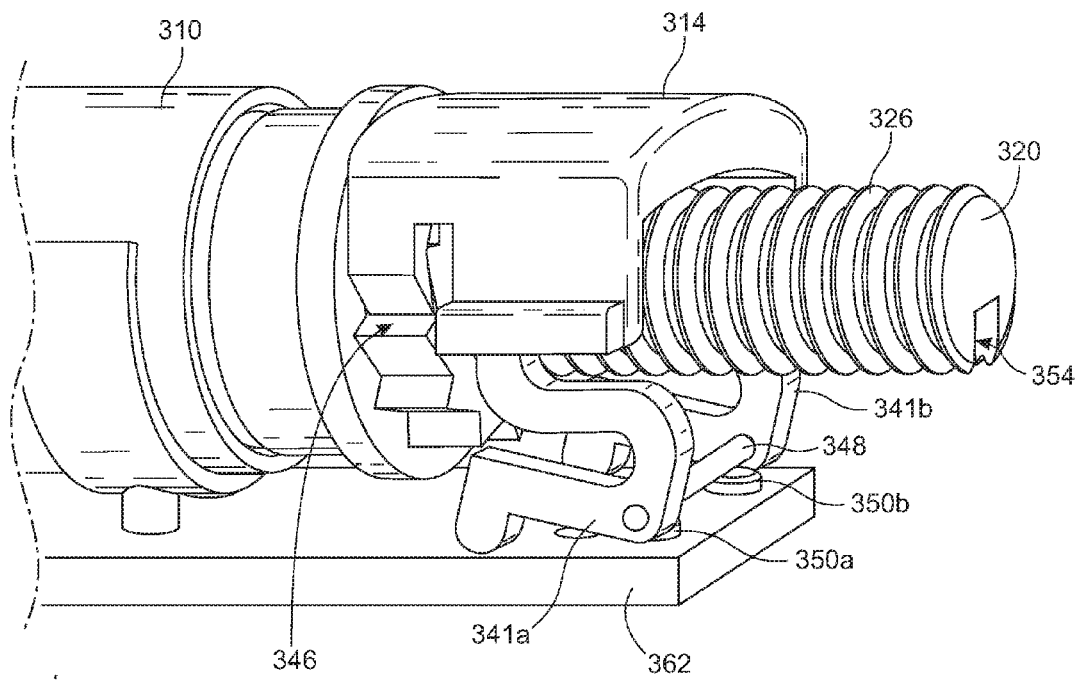
FIG. 31B is the medicant delivery device shown in FIG. 31A with the bottom depressed.

In some embodiments, the button 314 may function to initiate the delivery of power to the heating system 304 synchronous to the delivery of a bolus of medicant to the vaporization system 32. As shown in FIGS. 31A and 31B a contact pin 348 is provided spanning the button spring elements 341a, 341b. Deflection of the spring elements 341a, 341b during actuation of the button 314 lowers the contact pin 348 relative to contacts 350a, 350b, closing the circuit across the contacts 350a, 350b, as shown in FIG. 31B. This closure serves to initiate a power cycle to the vaporization system 32 as described later. In some embodiments, the contacts 350a, 350b may be directly under the spring elements 341a, 341b. The underside of the spring elements 341a, 341b may have independent contact pins 348 to connect with the contacts 350a, 350b to close the circuit. In some embodiments, a single contact pin 348 and a single contact 350a may be used.

Figure 32:
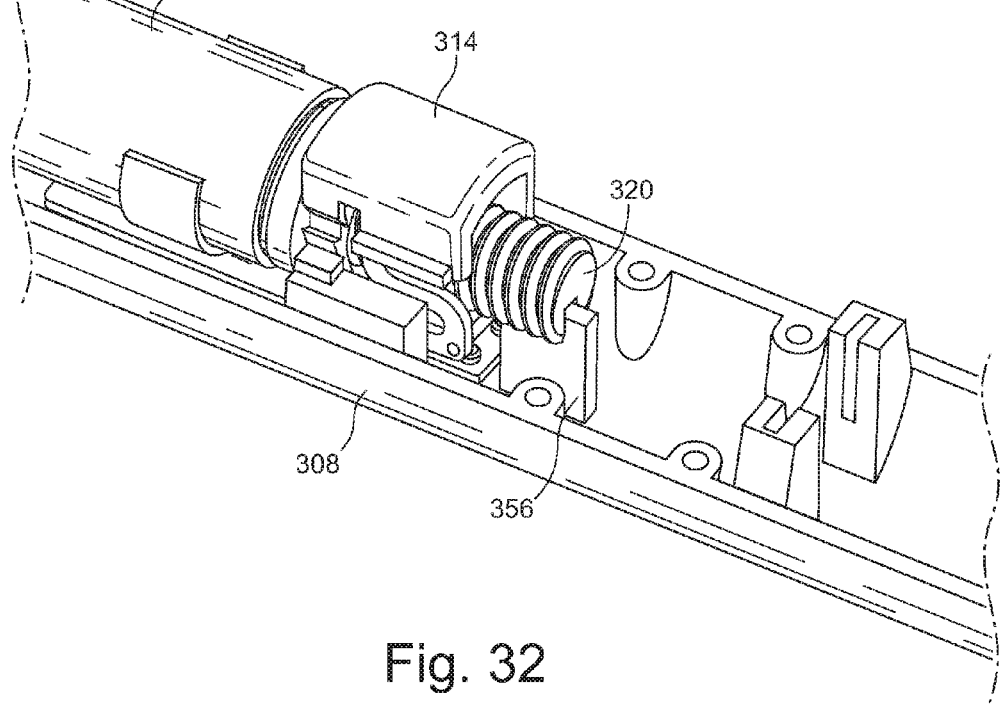
FIG. 32 is an isometric view of an embodiment of an anti-rotation feature of the fluid delivery system shown in FIG. 24.

The pitch of thread 326 is selected in consideration of the bore 352 of the reservoir 310, and controlled angular indexing of the drive nut 328 to displace the desired bolus of medicant from the reservoir 310 with each indexing of the drive nut 328. All of the rotational motions of the drive nut 328 are converted to linear motion on the plunger 320 to provide a consistent, fixed, and repeatable dose of the medicant. To ensure that the plunger 320 does not spin with the rotating drive nut 328, the plunger 320 is further provided with a groove 354 running down its length, said groove 354 accepting anti-rotation tang 356 protruding from the lower portion of the housing 308, as shown in FIG. 32.

The atomization or vaporization system 32, similar to what was described above, comprises a tightly coiled wire heater element 152 positioned adjacent to the fluid delivery system outlet 338. In the preferred embodiment, the coiled wire 152 is a nichrome wire. In some embodiments, the nichrome wire coil 152 may be wound around a high temperature fiber wicking element 360 to distribute the received medicant dose across the coil 152.

The power control system 34 comprises a circuit board 362 (containing the same or similar circuitry as described above) and associated battery 364 that delivers a fixed and precise amount of power to the nichrome wire 152 with each actuation, the amount of power delivered being that necessary to atomize or vaporize the precise volume of delivered bolus of the medicant. For optimal system efficiency, it is desirable to maximize energy density of the heater. Thus the coils of the heater are ideally spaced as close together as possible. Furthermore, it is desirable to distribute the dose of medicant that is to be vaporized as uniformly as possible across the heater elements. To that end, the heater coils 152 are wrapped around a wick 360 comprising material tolerant of high temperature, said material compelling the medicant to distribute evenly throughout the wick 360. The coil 152 is connected to the power control system 34 via crimp connectors 366. In the preferred embodiment, the circuit board 362 comprises a one-shot circuit (similar to or same as the circuitry described above) that delivers a fixed and precise amount of power to the nichrome heater 152 with each actuation, the amount of power delivered being that necessary to atomize the delivered bolus of medicant.

In some embodiments, to further provide a means for delivering a precise amount of power to the vaporization system 32, the power control system may comprise one or more supercaps 368*a*, 368*b* connected to the power source and the circuit. Using supercaps 368*a*, 368*b* prevents the vaporization system 32 from receiving varying amounts of power as the batteries 364 approach their end. In particular, supercaps 368*a*, 368*b* prevent the power to the vaporization system 32 from decreasing as the batteries die. Without the circuitry to precisely control the power, decreased battery power would lead to a lower temperature wire 152 for a given activation. In such case, if the volume of the medicant remains the same, then there may be incomplete vaporization of the medicant.

Figure 33:
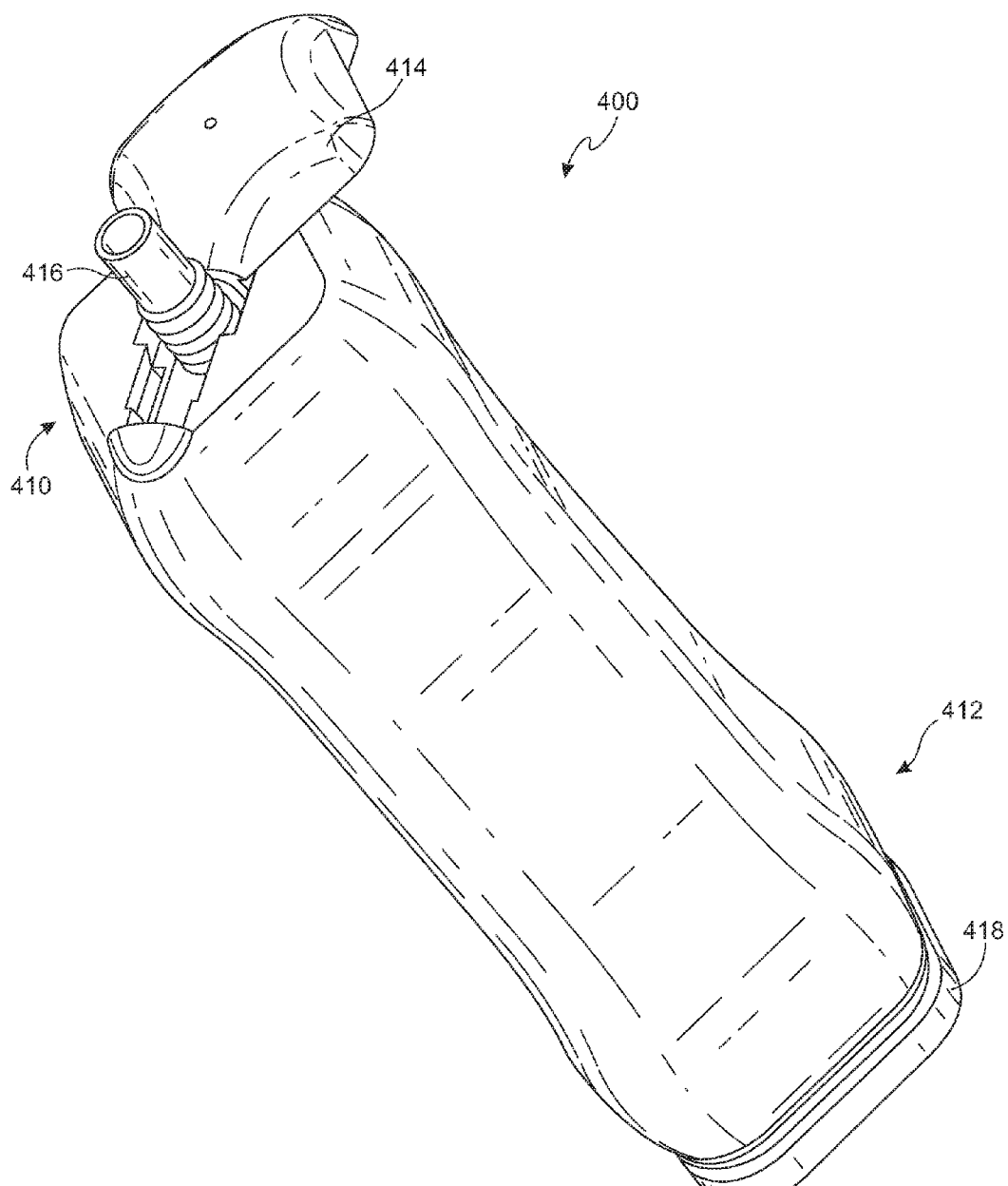
FIG. 33 is an isometric view of another embodiment of the delivery device.
Figure 34:
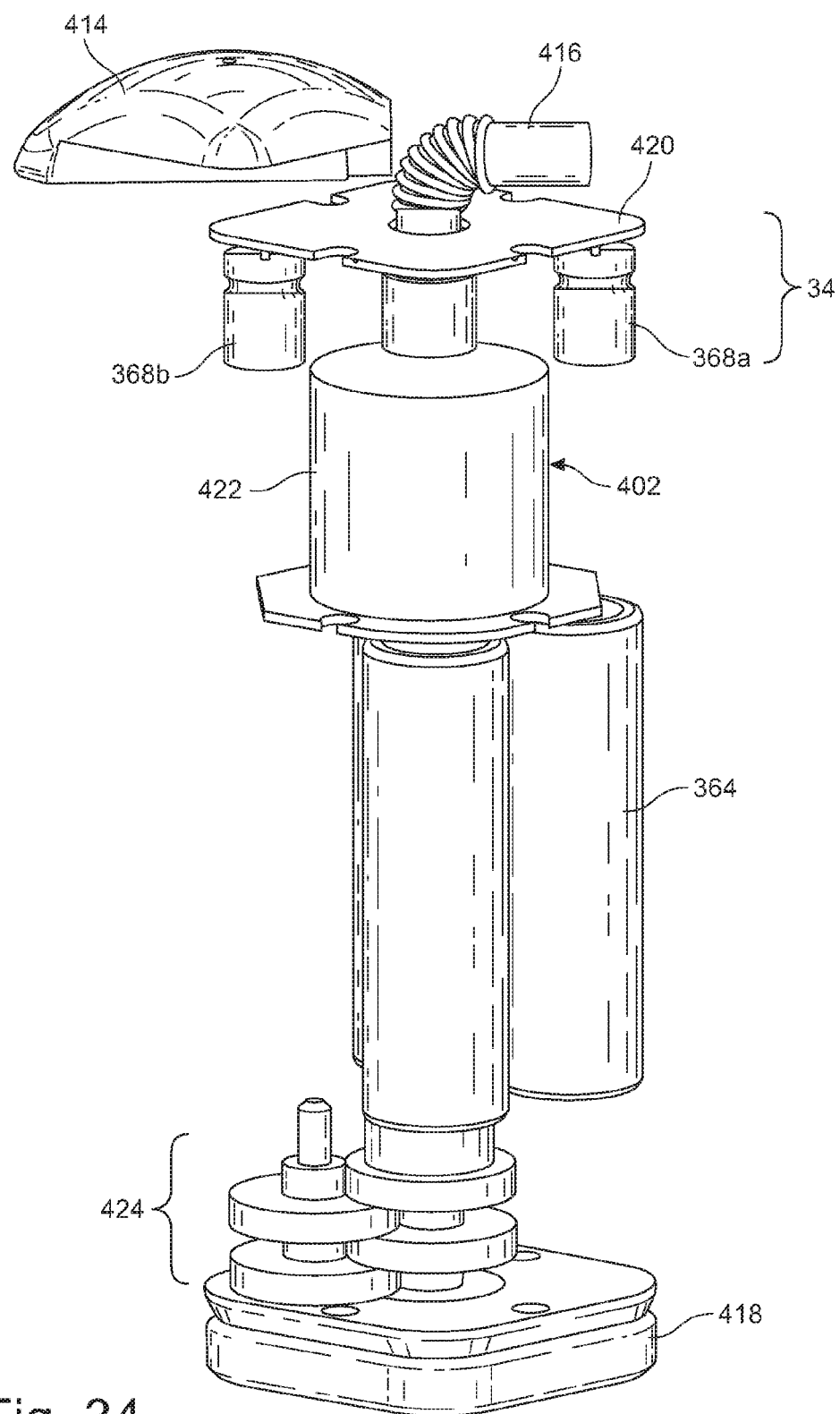
FIG. 34 is an isometric view of the delivery device shown in FIG. 33 with the housing removed.
Figure 35:
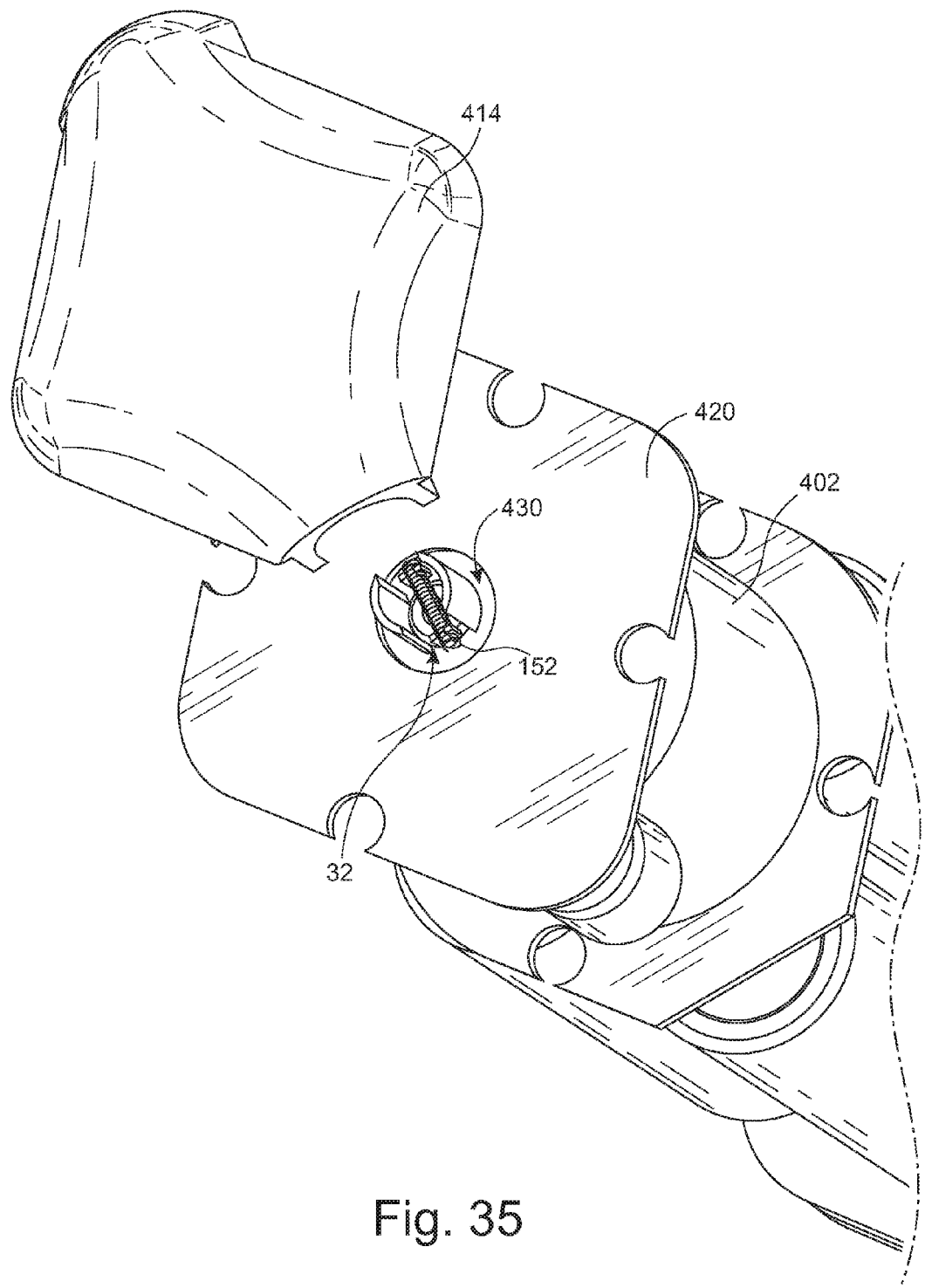
FIG. 35 is a close up view of the top of the delivery device shown in FIG. 33 showing the vaporization system.
Figure 36:
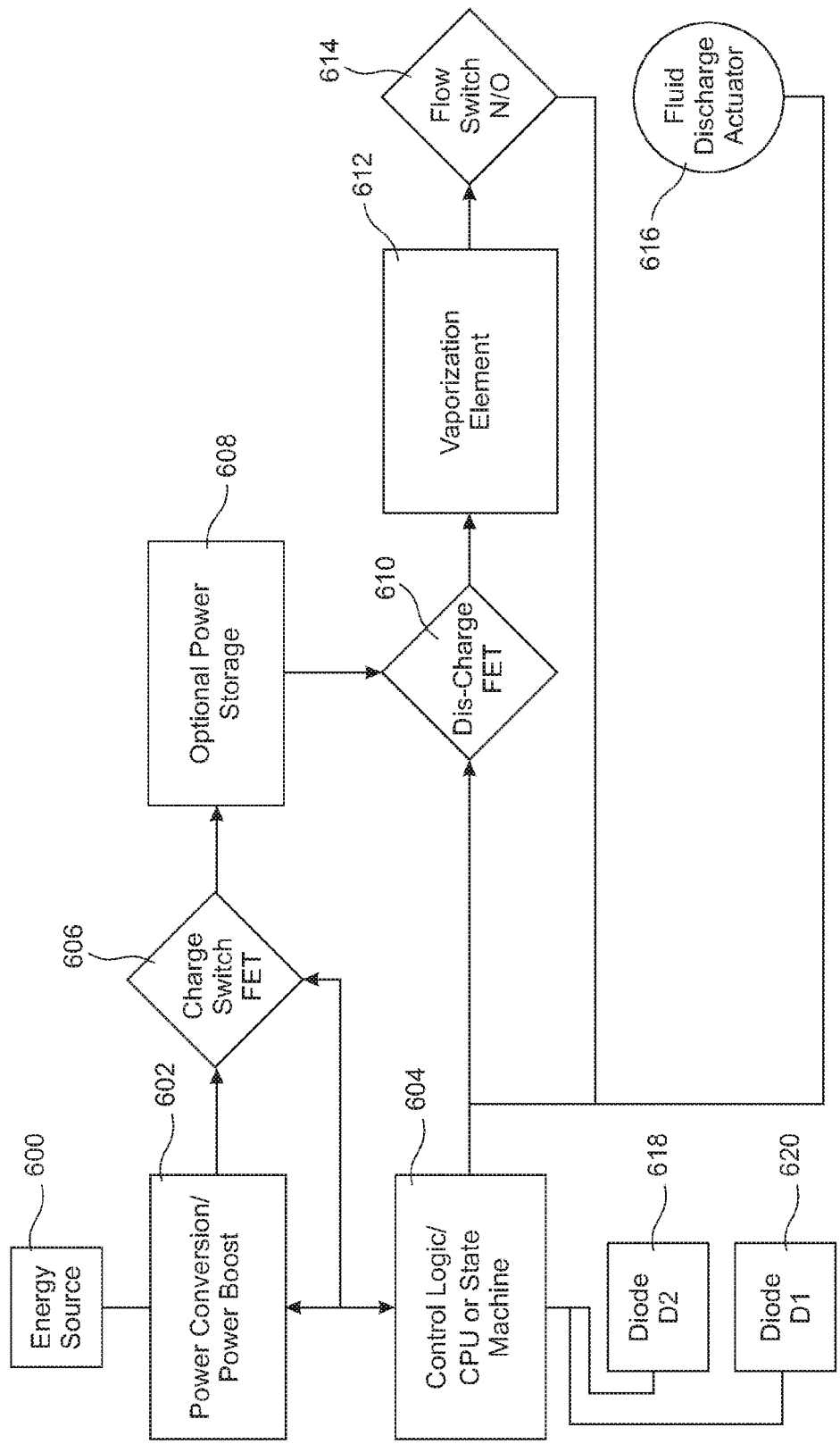
FIG. 36 is a block diagram of an embodiment of the power control system.

FIGS. 33-35 show another embodiment of a delivery device 400. FIG. 34 shows the delivery device 400 with the housing 408 removed. Delivery device 400 comprises the same or similar vaporization system 32 and power control system 34 as described above with another embodiment of a fluid delivery system 402 as a means for consistently metering a precise volume of a liquid from a fluid reservoir. The housing 408 of delivery device 400 also differs from that of delivery device 300. The housing 408 generally has an elongated box-like configuration. The housing 408 can take on other shapes as well, such as a cylinder or any shape or size desired for a particular application. The housing 408 has a top end 410 and a bottom and 412 opposite the top end 410. The top end 410 comprises a cover 414.

Protruding from the top end 410 is an inhaler tube 416. The inhaler tube 416 is operatively connected to the fluid delivery system 402. Medicants from the fluid delivery system 402 are vaporized by the vaporization system 32 and the vapors flow through the inhaler tube 416 and into the user's mouth. The cover 414 is used to protect the inhaler tube 416 when not in use. FIG. 33 shows a sliding cover; however, the cover 414 can be flip top, detachable, slidable, and the like. As the cover 414 is pushed back, away, off, or otherwise removed from the top and, the inhaler tube 416 is released and rotates upward. The user can there begin the process of inhaling through the inhaler, which starts the heating process by activating a flow sensor.

At the bottom end 412 of the housing 408 is a knob 418 to deliver a precise volume of medicant from the fluid delivery system 402 to the vaporization system 32. Like the button 314 of device 300, the knob 418 at the bottom 412 of device 400 is used to advance a plunger (not shown) through a syringe (not shown) repeatedly in a step-like manner to deliver precise, fixed, and consistent volume of a mendicant from the syringe and deposit it onto the coiled wire 152 of the vaporization system 32. Each rotation of the knob 418 advances an exact, metered amount of drug with a consistently repeatable volume.

Like the previous versions, the device 400 utilizes a circuit board 420 (containing the same or similar circuitry as described above for the power control system 34) with associated processor (not shown), super caps 368*a*, 368*b*, and other electronic components utilized to deliver a consistent, precise and sufficient amount of power to the heating system to vaporize or atomize a predetermined volume of a liquid. The circuit board 420 is located at the top end 410 adjacent to the fluid delivery system 402 and the vaporization system 32. A through-hole 430 is provided to allow the inhaler tube 416 to be passed through the circuit board 420 allowing the fluid reservoir 422 to be attached to this inhaler tube 416 and present the inhaler tube 416 to the user.

Below the circuit board 420, the fluid delivery system 402 is mounted. This assembly provides a secure, tamper resistant chamber for retaining the fluid. The fluid delivery system 402 is then connected to a gear reduction assembly 424 that allows the linear syringe actuator to be advanced through the reservoir 422 in a consistent amount for each rotation of the knob 418.

The vaporization system 32 is placed into the path of the fluid that is delivered via the fluid delivery system 402 each time the knob 418 is rotated. The vaporization 32 comprises a heating coil 152. In some embodiments, the heating coil 152 may be wrapped around a wick 360, which helps retain the liquid after it has been discharged from the fluid delivery system 402. After the fluid is advanced, the fluid wets the wick 428 that is placed inside the heating coil assembly 152. Once this wick 360 is wetted, the coil 152 can be heated once the user begins to inhale (suck) on the inhaler tube 416. To trigger the heating mechanism, a flow sensor (not shown) is placed in the inhalation path, which is the path between the inlet of the inhaler tube 416 and the outlet 417 of the inhaler tube 416.

As flow is sensed when the user begins to inhale/suck on the inhaler tube 416, the coil heating is begun by applying voltage to the coil 152. The power applied to the coil wire 152 is supplied via the supercap assembly 368*a*, 368*b*, which is charged via the device batteries 364.

To further improve the delivery and efficacy of the medicant delivered by the present invention, plume chemistry of the medicant delivered to the lungs must be analyzed. Depending on the size of the vapor product released by the vapor delivery device, the medicant may have effects at various places; thereby dictating the effectiveness and speed with which the medicant can work on a user. For example, the larger vapor products are more likely to get caught inside the mouth, which would result in the medicant travelling through the digestive track. Small vapor products can be inhaled into the lungs, but may get caught in the upper lungs. Even finer vapor products can reach the lower lungs where absorption of the medicant is more effective and faster.

Again, to control the size of the vapor product, a permeable membrane of ceramic, fabric, or the like may be placed between the heating system and the mouthpiece. The heating element allows the medicant to vaporize; however, prior to exiting through the mouthpiece, the vapor product is filtered through the permeable membrane to govern the size of the vapor product delivered to the user. The membrane should be made of a material that is resilient to heat, such as ceramic or Kevlar® material.

Due to the consistent, reliable, and precise control of dosage offered by the present invention, its application goes far beyond just as a substitute for tobacco products. The device can be used to deliver dietary supplements, sleep aids, weight loss products, pain killers, and many other prescription or over-the-counter pharmaceutical products where precise dosing is required. The present invention can even be implemented in a non-pharmaceutical context, such as for dispensing liquid candies for consumption, breath fresheners, room fresheners, and any other application where vaporization of a liquid in consistent, reliable, and precise doses are needed.

While the system and device have been described in terms of what are presently considered to be the most practical and effective embodiments, it is to be understood that the disclosure need not be limited to the disclosed embodiments. It is intended that all permutations, enhancements, equivalents, combinations, and improvements thereto that are apparent to those skilled in the art upon a reading of the specification and a study of the drawings are included within the true spirit and scope of the present invention. The scope of the disclosure should thus be accorded the broadest interpretation so as to encompass all such modifications and similar structures. It is therefore intended that the application includes all such modifications, permutations and equivalents that fall within the true spirit and scope of the present invention. Thus, multiple embodiments and methods have been shown and described. Various modifications and substitutions may of course be made without departing from the spirit and scope of the invention. The invention, therefore, should not be limited except by the following claims and their equivalents.

INDUSTRIAL APPLICABILITY

This invention may be industrially applied to the development, manufacture, and use of a medicant delivery system that can consistently, reliably, and repeatably deliver a precise dose of a medicant to a user in vapor form in an energy efficient manner. The delivery system comprises a power control system, a vaporization system, and a fluid delivery system. The power control system utilizes a circuitry that allows the system to deliver just enough power to vaporize or atomize a known volume of a medicant. To avoid changes in the current due to power age, the control system utilizes supercapacitors connected to the circuitry. The power source and/or the resistance at the heating element can be monitored so that the system knows how march power needs to be supplied to efficiently vaporize the known volume of medicant. The fluid delivery system utilizes a reservoir and dispensing mechanism at dispenses the same volume of medicant with each actuation. The heating system utilizes nichrome wire.

What is claimed is:

1. A control system for a hand-held vapor delivery device, comprising: a circuit configured to provide a precise amount of power from a power source to heat a heating element to a minimum required temperature to completely vaporize a precise volume of a liquid, and control a precise duration of time to supply the precise amount of power to completely vaporize the predetermined volume of liquid at the required temperature;

monitor a temperature of the heating element while the power is being supplied;

compare the temperature of the heating element to the minimum required temperature; and adjust the precise duration of time or the precise amount of power based on the comparison step to completely vaporize the liquid, wherein if the precise volume of liquid is adjusted, the precise duration of time or the precise amount of power is adjusted to completely vaporize the adjusted precise volume of liquid within a new minimum required temperature for a new minimum required time.

2. The control system of claim 1, wherein the circuit comprises a one-shot circuit.

3. The control system of claim 1, wherein the circuit further comprises a processor programmed to monitor a resistance of the heating element and adjust the amount of power to a level sufficient to heat the heating element to the required temperature.

4. The control system of claim 1, wherein the circuit comprises a DC/DC boost converter and a supercapacitor operatively connected to the power source to adjust the amount of power to the level sufficient to heat the heating element to the required temperature.

5. The control system of claim 1, wherein the circuit is configured to actuate the power source a predetermined number of times.

6. A control system for a hand-held vapor delivery device, comprising:

a. a means for providing a precise amount of power from a power source to heat a heating element to a minimum required temperature to completely vaporize a precise volume of a liquid; and b. a means for controlling a precise duration of time to supply the precise amount of power to completely vaporize the predetermined volume of liquid at the required temperature, wherein the precise duration of time or the precise amount of power is adjusted based on a comparison of a temperature of the heating element to the minimum required temperature to completely vaporize the liquid, wherein if the precise volume of liquid is adjusted, the precise duration of time or the precise amount of power is adjusted to completely vaporize the adjusted precise volume of liquid within a new minimum required temperature for a new minimum required time.

* * * * *